(12) United States Patent
Aronov et al.

(10) Patent No.: US 7,314,885 B2
(45) Date of Patent: Jan. 1, 2008

(54) PYRROLE COMPOUNDS USEFUL AS KINASE INHIBITORS

(75) Inventors: Alex Aronov, Watertown, MA (US); Upul K. Bandarage, Lexington, MA (US); David J. Lauffer, Stow, MA (US); Pan Li, Arlington, MA (US); Ronald C. Tomlinson, Sudbury, MA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days.

(21) Appl. No.: 11/387,126

(22) Filed: Mar. 22, 2006

(65) Prior Publication Data

US 2006/0173055 A1    Aug. 3, 2006

Related U.S. Application Data

(63) Continuation of application No. 10/919,774, filed on Aug. 16, 2004, now abandoned.

(60) Provisional application No. 60/495,535, filed on Aug. 15, 2003.

(51) Int. Cl.
| | |
|---|---|
| A61K 31/41 | (2006.01) |
| A61K 31/4168 | (2006.01) |
| A61K 31/4025 | (2006.01) |
| A61K 31/341 | (2006.01) |
| C07D 207/36 | (2006.01) |
| C07D 257/04 | (2006.01) |
| C07D 307/06 | (2006.01) |

(52) U.S. Cl. ............ 514/382; 514/397; 514/422; 514/471; 548/518; 548/253; 548/560; 548/563; 549/473

(58) Field of Classification Search ........... 514/381, 514/382, 422, 423, 385, 277; 548/250, 253, 548/518, 335.1; 544/333; 546/1
See application file for complete search history.

(56) References Cited

FOREIGN PATENT DOCUMENTS

| | | |
|---|---|---|
| WO | WO 01/56557 A2 | 8/2001 |
| WO | WO 01/57022 A2 | 8/2001 |
| WO | WO 02/22610 A1 | 3/2002 |
| WO | WO 02/088097 A1 | 11/2002 |
| WO | WO 03/011855 A2 | 2/2003 |

OTHER PUBLICATIONS

Morotti et al., Oncogene, 2002, vol. 21, p. 4885-4893.*

* cited by examiner

*Primary Examiner*—Rebecca Anderson
*Assistant Examiner*—Yong Chu
(74) *Attorney, Agent, or Firm*—Daniel A. Pearson; Karen E. Brown

(57) ABSTRACT

The present invention relates to compounds useful of inhibitors of protein kinases. The invention also provides pharmaceutically acceptable compositions comprising said compounds, processes for making the compounds and methods of using the compositions in the treatment of various disease, conditions, or disorders.

14 Claims, No Drawings

US 7,314,885 B2

PYRROLE COMPOUNDS USEFUL AS KINASE INHIBITORS

CROSS-REFERENCE TO RELATED APPLICATIONS

The present application is a continuation of U.S. patent application Ser. No. 10/919,774, filed Aug. 16, 2004, now abandoned, which claims the benefit of U.S. Provisional Application 60/309,886, filed Aug. 15, 2003, the entire contents of both applications incorporated herein by reference.

TECHNICAL FIELD OF THE INVENTION

The present invention relates to compounds useful as inhibitors of c-Met protein kinase. The invention also provides pharmaceutically acceptable compositions comprising the compounds of the invention, processes for making the compounds, and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, cancer and other proliferative disorders. Accordingly, there has been a substantial effort in medicinal chemistry to find protein kinase inhibitors that are effective as therapeutic agents.

The c-Met proto-oncogene encodes the Met receptor tyrosine kinase. The Met receptor is a 190 kDa glycosylated dimeric complex composed of a 50 kDa alpha chain disulfide-linked to a 145 kDa beta chain. The alpha chain is found extracellularly while the beta chain contains transmembrane and cytosolic domains. Met is synthesized as a precursor and is proteolytically cleaved to yield mature alpha and beta subunits. It displays structural similarities to semaphorins and plexins, a ligand-receptor family that is involved in cell-cell interaction. The ligand for Met is hepatocyte growth factor (HGF), a member of the scatter factor family and has some homology to plasminogen [Longati, P. et al., *Curr. Drug Targets* 2001, 2, 41-55); Trusolino, L. and Comoglio, P. *Nature Rev. Cancer* 2002, 2, 289-300].

Met functions in tumorigenesis and tumor metastasis. Chromosomal rearrangements forming Tpr-met fusions in an osteoclast cell line resulted in constitutively active Met receptors and transformation (Cooper, C. S. et al., *Nature* 1984, 311, 29-33). Met mutants exhibiting enhanced kinase activity have been identified in both hereditary and sporadic forms of papillary renal carcinoma (Schmidt, L. et al., *Nat. Genet.* 1997, 16, 68-73; Jeffers, M. et al., *Proc. Nat. Acad. Sci.* 1997, 94, 11445-11500). Expression of Met along with its ligand HGF is transforming, tumorigenic, and metastatic (Jeffers, M. et al., *Oncogene* 1996, 13, 853-856; Michieli, P. et al., *Oncogene* 1999, 18, 5221-5231). HGF/Met has been shown to inhibit anoikis, suspension-induced programmed cell death (apoptosis), in head and neck squamous cell carcinoma cells. Anoikis resistance or anchorage-independent survival is a hallmark of oncogenic transformation of epithelial cells (Zeng, Q. et al., *J. Biol. Chem.* 2002, 277, 25203-25208).

MET is overexpressed in a significant percentage of human cancers and is amplified during the transition between primary tumors and metastasis. To investigate whether this oncogene is directly responsible for the acquisition of the metastatic phenotype, Giordano et al. exploited a single-hit oncogenic version of MET that was able to transform and to confer invasive and metastatic properties to nontumorigenic cells, both in vitro and in nude mice. They found a point mutation in the signal transducer docking site of MET that increased the transforming ability of the oncogene, but abolished its metastatic potential. They concluded that the metastatic potential of the MET oncogene relies on the properties of its multifunctional docking site, and that a single point mutation affecting signal transduction can dissociate neoplastic transformation from metastasis. Giordano, S., et al, *Proc. Nat. Acad. Sci.* 94: 13868-13872, 1997.

c-Met is implicated in various cancers, especially renal cancer. It was found that the beta-subunit of the c-Met protooncogene product is the cell-surface receptor for hepatocyte growth factor. It was also identified that the hepatocyte growth factor receptor is the c-met proto-oncogene product. Bottaro, D. P., et al, *Science* 251: 802-804, 1991.

HGF/Met signaling is involved in cell adhesion and motility in normal cells and plays a major role in the invasive growth that is found in most tissues, including cartilage, bone, blood vessels, and neurons (reviewed in Comoglio, P. M. and Trusolino, L. *J. Clin. Invest.* 2002, 109, 857-862). Dysfunctional activation or increased numbers of Met is likely to contribute to the aberrant cell-cell interactions that lead to migration, proliferation, and survival of cells that is characteristic of tumor metastasis. Activation of Met induces and sustains a variety of tumors [Wang, R. et al., *J. Cell. Biol.* 2001, 153, 1023-1034; Liang, T. J. et al., *J. Clin. Invest.* 1996, 97, 2872-2877; Jeffers, M. et al., *Proc. Nat. Acad. Sci.* 1998, 95, 14417-14422] while loss of Met inhibits growth and invasiveness of tumor cells [Jiang, W. G. et al., *Clin. Cancer Res.* 2001, 7, 2555-2562; Abounader, R. et al., *FASEB J.* 2002 16, 108-110]. Increased expression of Met/HGF is seen in many metastatic tumors including colon (Fazekas, K. et al., *Clin. Exp. Metastasis* 2000, 18, 639-649), breast (Elliott, B. E. et al., 2002, *Can. J. Physiol. Pharmacol.* 80, 91-102), prostate (Knudsen, B. S. et al., *Urology* 2002, 60, 1113-1117), lung (Siegfried, J. M. et al., *Ann. Thorac. Surg.* 1998, 66, 1915-1918), and gastric (Amemiya, H. et al., *Oncology* 2002, 63, 286-296).

Further demonstration of the role Met plays in metastasis was shown by Giordano, et al. (2002) who presented evidence for cross-talk between the semaphorin 4D (SEMA4D; 601866) receptor, plexin B1 (PLXNB1; 601053), and MET during invasive growth in epithelial cells. Binding of SEMA4D to PLXNB1 stimulated tyrosine kinase activity of MET, resulting in tyrosine phosphorylation of both receptors. This effect was not found in cells lacking MET expression. Giordano, S., et al: The Semaphorin 4D receptor controls invasive growth by coupling with Met. *Nature Cell Biol.* 4: 720-724, 2002.

HGF-Met signaling has also been associated with increased risk of atherosclerosis (Yamamoto, Y. et al., *J. Hypertens.* 2001, 19, 1975-1979; Morishita, R. et al., *Endocr. J.* 2002, 49, 273-284) and increased fibrosis of the lung (Crestani, B. et al., *Lab. Invest.* 2002, 82, 1015-1022.

Accordingly, there is a great need to develop compounds useful as inhibitors of protein kinases. In particular, it would be desirable to develop compounds that are useful as inhibitors of c-Met, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of c-Met protein kinase. These compounds have the general formula I:

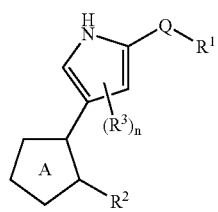

I or a pharmaceutically acceptable salt thereof, wherein Ring A, $R^1$, $R^2$, and Q are as defined below.

These compounds and pharmaceutically acceptable compositions thereof are useful for treating or preventing a variety of diseases, disorders or conditions, including, but not limited to, cancer and other proliferative disorders.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention:

The present invention relates to a compound of formula I:

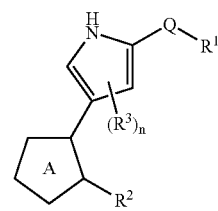

I or a pharmaceutically acceptable salt thereof, wherein:

Q is a $C_{1-6}$ alkylidene chain wherein one methylene unit of Q is replaced by —C(O)N(R)—, —C(O)—, —C(O)O—, —N(R)—, —O—, —S—, —SO$_2$—, or —SO$_2$N(R)—;

each R is independently hydrogen or an optionally substituted $C_{1-6}$ aliphatic group, wherein:

two R groups on the same nitrogen atom are optionally taken together with said nitrogen atom to form an optionally substituted 3-7 membered saturated, partially unsaturated, or fully unsaturated ring having 1-3 heteroatoms independently selected from nitrogen, oxygen, or sulfur;

$R^1$ is H, —N(R)$_2$, or an optionally substituted ring selected from a 3-7 membered saturated or partially unsaturated ring having 0-3 heteroatoms independently selected from nitrogen, oxygen, or sulfur, a 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur;

$R^2$ is an optionally substituted 6-membered aryl ring having 0-3 nitrogens;

each $R^3$ is independently R, CN, NO$_2$, halogen, N(R)$_2$, OR, or SR;

n is 0-2; and

Ring A is an optionally substituted ring selected from:

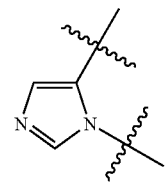

a

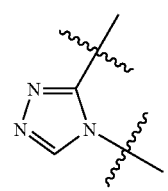

b

-continued

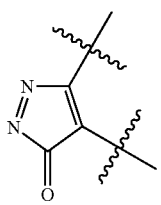

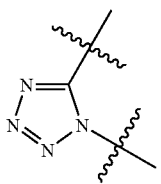

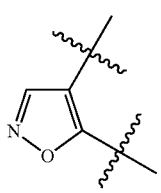

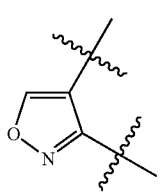

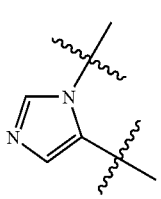

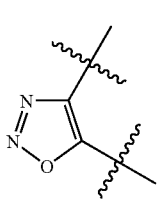

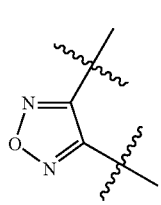

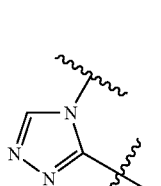

-continued

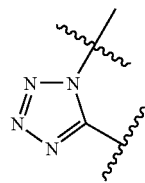

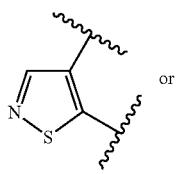

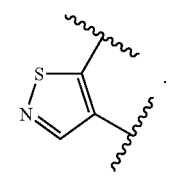

The present invention also relates to a compound of formula I:

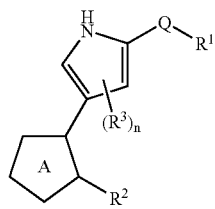

I or a pharmaceutically acceptable salt thereof, wherein:

Q is a $C_{1-6}$ alkylidene chain wherein one methylene unit of Q is replaced by —C(O)N(R)—, —C(O)—, —C(O)O—, —N(R)—, —O—, —S—, —SO$_2$—, or —SO$_2$N(R)—;

each R is independently hydrogen or an optionally substituted $C_{1-6}$ aliphatic group, wherein:
  two R groups on the same nitrogen atom are optionally taken together with said nitrogen atom to form an optionally substituted 3-7 membered saturated, partially unsaturated, or fully unsaturated ring having 1-3 heteroatoms independently selected from nitrogen, oxygen, or sulfur;

$R^1$ is H, —N(R)$_2$, or an optionally substituted ring selected from a 3-7 membered saturated or partially unsaturated ring having 0-3 heteroatoms independently selected from nitrogen, oxygen, or sulfur, a 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur;

$R^2$ is an optionally substituted 6-membered aryl ring having 0-3 nitrogens;

each $R^3$ is independently R, CN, NO$_2$, halogen, N(R)$_2$, OR, or SR;

n is 0-2; and

Ring A is an optionally substituted ring selected from:

a 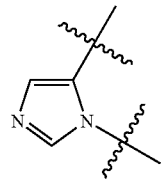

b 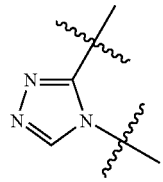

c 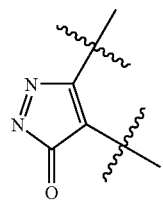

d 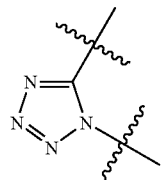

e 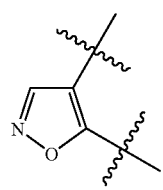

f 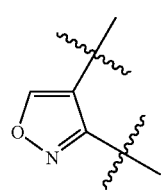

g 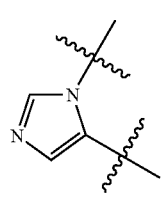

h 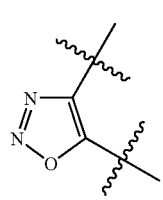

i 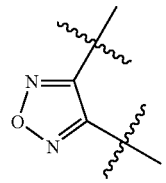

j 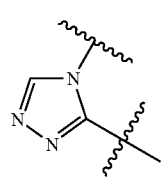

k 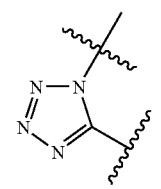

l 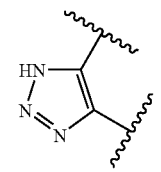

m 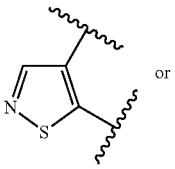

or n 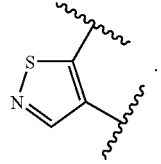

.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, alkyl, alkenyl, alkynyl, cycloalkyl, cycloalkenyl, cycloalkynyl groups and hybrids thereof such as (cycloalkyl)alkyl, (cycloalkenyl)alkyl or (cycloalkyl)alkenyl.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —$R^\circ$; —$OR^\circ$; —$SR^\circ$; 1,2-methylenedioxy; 1,2-ethylenedioxy; phenyl (Ph) optionally substituted with $R^\circ$; —O(Ph) optionally substituted with $R^\circ$; —$(CH_2)_{1-2}$(Ph), optionally substituted with $R^\circ$; —CH═CH(Ph), optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2R^\circ$; —$NR^\circ NR^\circ C(O)R^\circ$; —$NR^\circ NR^\circ C(O)N(R^\circ)_2$; —$NR^\circ NR^\circ CO_2R^\circ$; —$C(O)C(O)R^\circ$; —$C(O)CH_2C(O)R^\circ$; —$CO_2R^\circ$; —$C(O)R^\circ$; —$C(S)R^\circ$; —$C(O)N(R^\circ)_2$; —$C(S)N(R^\circ)_2$; —$OC(O)N(R^\circ)_2$; —$OC(O)R^\circ$; —$C(O)N(OR^\circ)R^\circ$; —$C(NOR^\circ)R^\circ$; —$S(O)_2R^\circ$; —$S(O)_3R^\circ$; —$SO_2N(R^\circ)_2$; —$S(O)R^\circ$; —$NR^\circ SO_2N(R^\circ)_2$; —$NR^\circ SO_2R^\circ$; —$N(OR^\circ)R^\circ$; —C(═NH)—$N(R^\circ)_2$; or —$(CH_2)_{0-2}NHC(O)R^\circ$ wherein each independent occurrence of $R^\circ$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^\circ$, on the same substituent or different substituents, taken together with the atom(s) to which each $R^\circ$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of $R^\circ$ are selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}$ aliphatic), or $haloC_{1-4}aliphatic$, wherein each of the foregoing $C_{1-4}aliphatic$ groups of $R^\circ$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo ($C_{1-4}$ aliphatic), wherein each of the foregoing $C_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo ($C_{1-4}$ aliphatic), wherein each of the foregoing $C_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R$^o$ (or R$^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R$^o$ (or R$^+$, or any other variable similarly defined herein) are taken together with the atom(s) to which each variable is bound include, but are not limited to the following: a) two independent occurrences of R$^o$ (or R$^+$, or any other variable similarly defined herein) that are bound to the same atom and are taken together with that atom to form a ring, for example, N(R$^o$)$_2$, where both occurrences of R$^o$ are taken together with the nitrogen atom to form a piperidin-1-yl, piperazin-1-yl, or morpholin-4-yl group; and b) two independent occurrences of R$^o$ (or R$^+$, or any other variable similarly defined herein) that are bound to different atoms and are taken together with both of those atoms to form a ring, for example where a phenyl group is substituted with two occurrences of OR$^o$

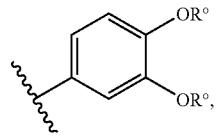

these two occurrences of R$^o$ are taken together with the oxygen atoms to which they are bound to form a fused 6-membered oxygen containing ring:

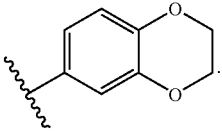

It will be appreciated that a variety of other rings can be formed when two independent occurrences of R$^o$ (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds:

According to one embodiment, the present invention relates to a compound of formula I wherein Q is —C(O)—.

According to another embodiment, Q is —C(O)N(R)—.

Another aspect of the present invention relates to a compound of formula I wherein R$^1$ is an optionally substituted ring selected from a 3-7 membered saturated or partially unsaturated ring having 0-3 heteroatoms independently selected from nitrogen, oxygen, or sulfur, a 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur.

According to another embodiment, R$^1$ is a 4-6 membered saturated ring having 0-3 heteroatoms independently selected from nitrogen, oxygen, or sulfur. Such rings include cyclopentyl, cyclohexyl, tetrahydrofuranyl, pyrrolidin-1-yl, morpholin-4-yl, thiomorpholin-4-yl, piperidin-1-yl, and azetidin-1-yl.

According to another embodiment, R$^1$ is a 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur.

According to another embodiment, R¹ is as depicted in the compounds of I-1 to I-47.

Another aspect of the present invention relates to a compound of formula I wherein n is 0 or n is 1.

Yet another aspect of the present invention relates to a compound of formula I wherein R² is an optionally substituted phenyl ring. Examples of substituents on the R² phenyl ring, when present, include chloro and fluoro.

According to another embodiment, the present invention relates to a compound of formula I wherein R² is an optionally subsituted pyridyl or pyrimidinyl ring.

Another embodiment of the present invention relates to a compound of formula I wherein Ring A is an optionally substituted ring selected from:

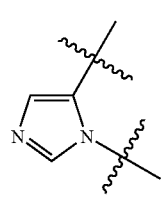
a

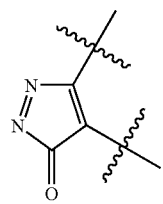
c

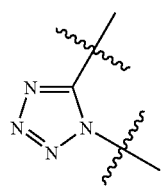
d

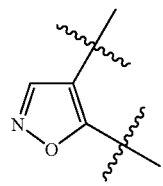
e

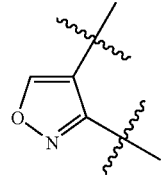
f

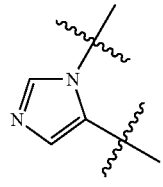
g

-continued

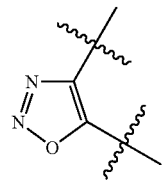
h

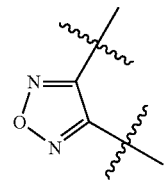
i

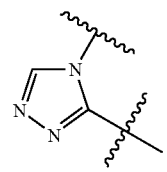
j

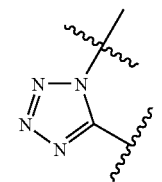
k

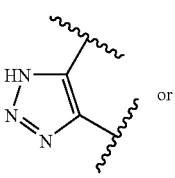
l      or

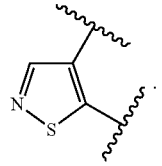
m

Another embodiment of the present invention relates to a compound of formula I wherein Ring A is an optionally substituted ring selected from:

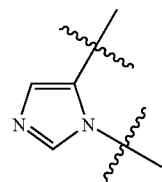
a

-continued c 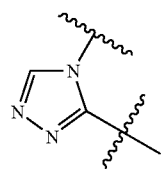

d 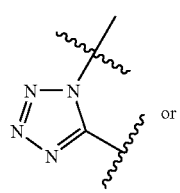

e 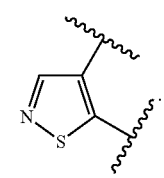

According to one embodiment, the present invention relates to a compound of formula I wherein Ring A is unsubstituted.

According to another embodiment, the present invention relates to a compound of formula I wherein Ring A is optionally substituted with oxo, —OH, —NH$_2$, or —CH$_3$.

Exemplary structures of formula I are set forth in Table 1, below. In specific embodiments, the variables are as depicted in these structures.

TABLE 1

Examples of Compounds of Formula I:

I-1
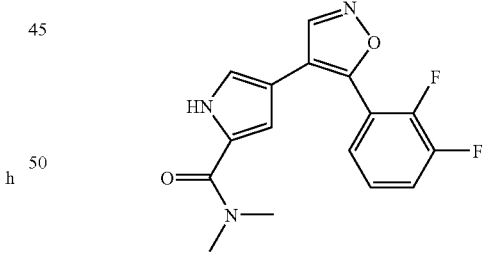

I-2
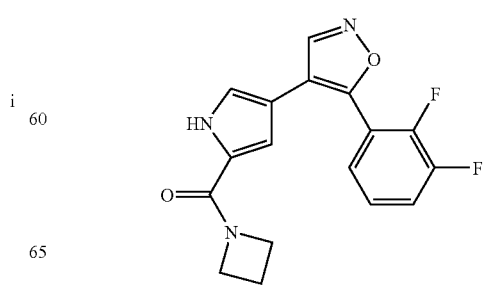

-continued j 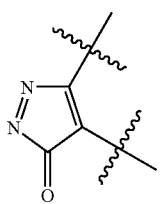

k 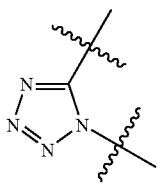 or m 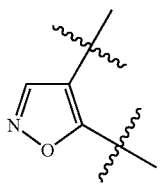

e 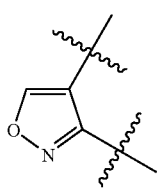

f 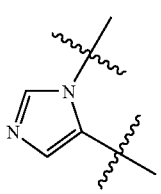

g 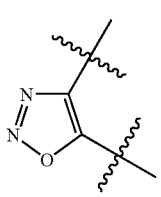

h 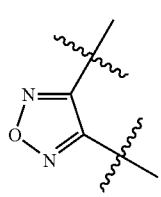

i

TABLE 1-continued
Examples of Compounds of Formula I:
I-3
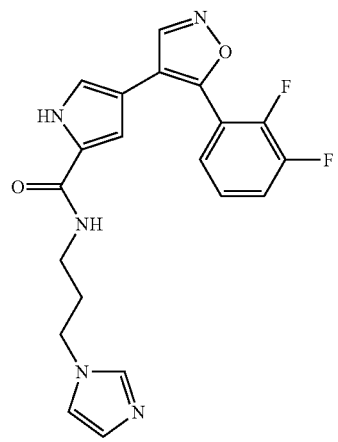
I-4
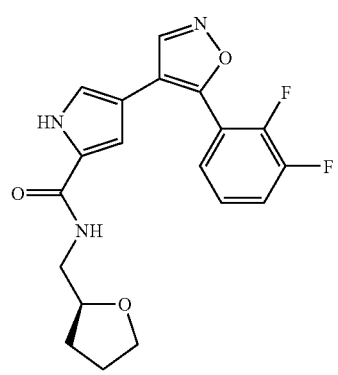
I-5
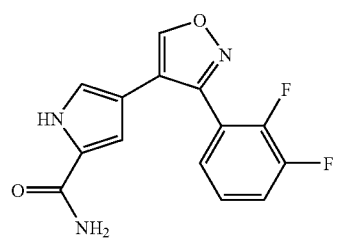
I-6
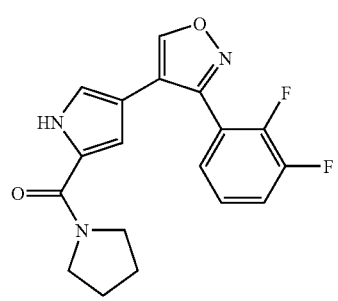
TABLE 1-continued
Examples of Compounds of Formula I:
I-7
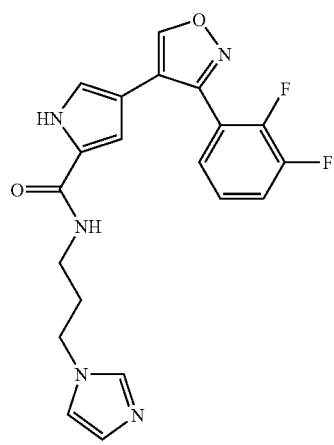
I-8
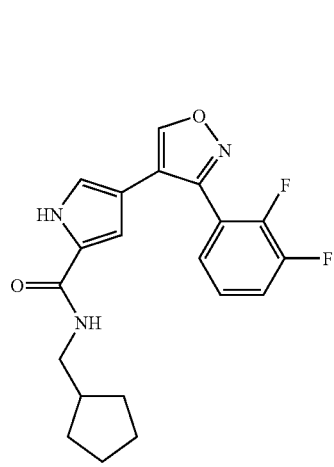
I-9
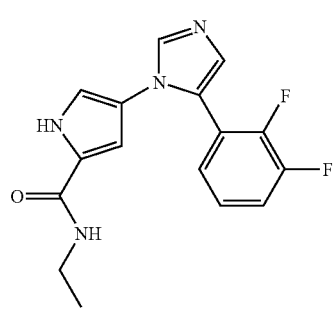

TABLE 1-continued
Examples of Compounds of Formula I:
I-10
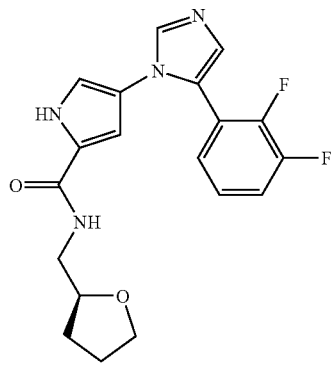
I-11
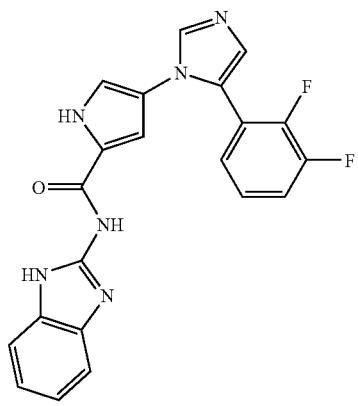
I-12
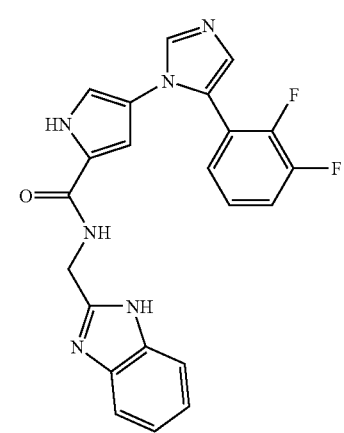
TABLE 1-continued
Examples of Compounds of Formula I:
I-13
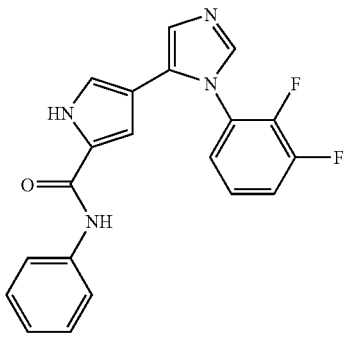
I-14
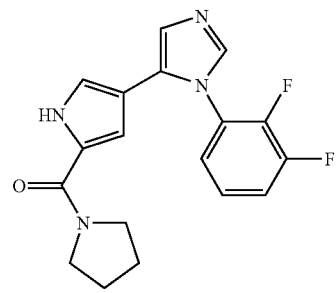
I-15
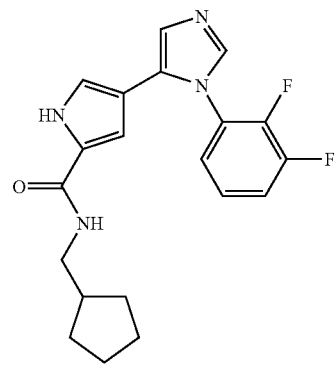
I-16
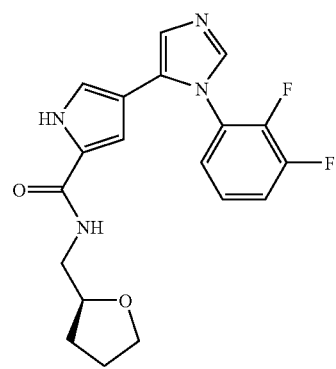

TABLE 1-continued
Examples of Compounds of Formula I:
I-17
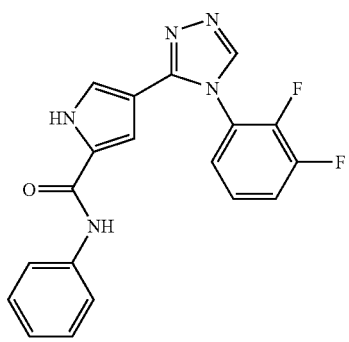
I-18
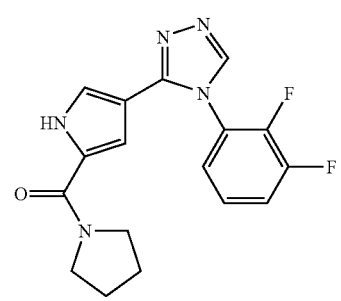
I-19
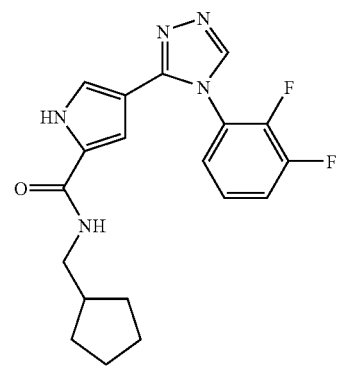
I-20
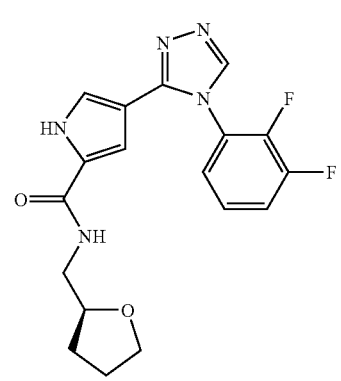
TABLE 1-continued
Examples of Compounds of Formula I:
I-21
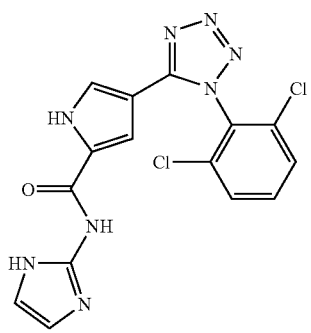
I-22
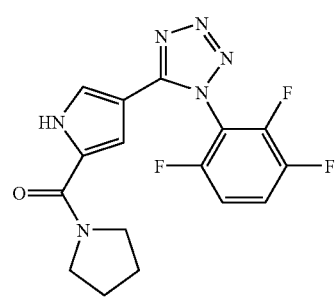
I-23
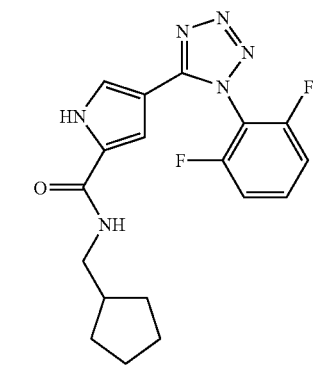
I-24
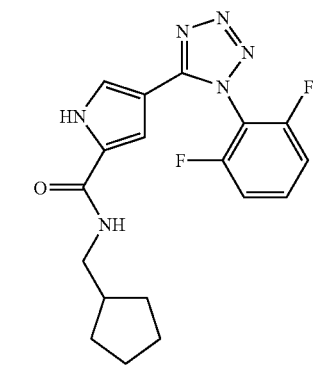

TABLE 1-continued
Examples of Compounds of Formula I:
I-25
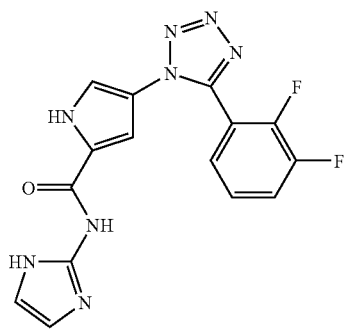
I-26
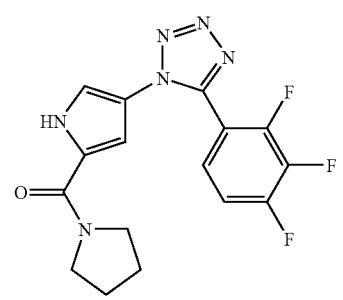
I-27
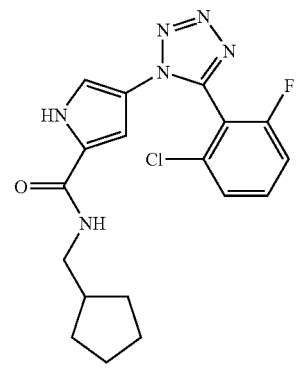
I-28
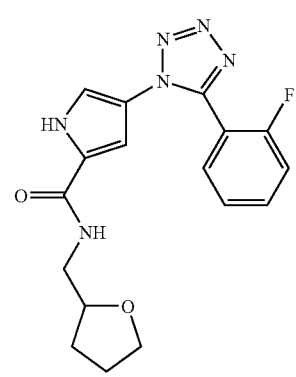
TABLE 1-continued
Examples of Compounds of Formula I:
I-29
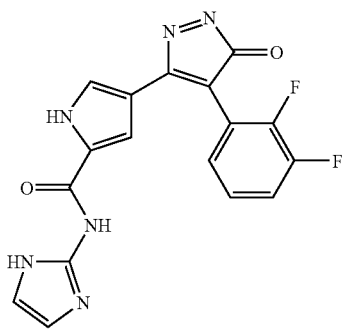
I-30
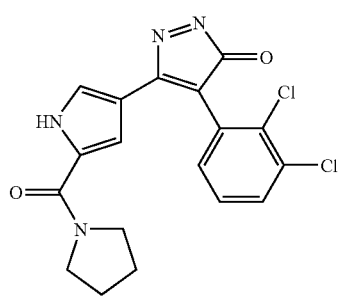
I-31
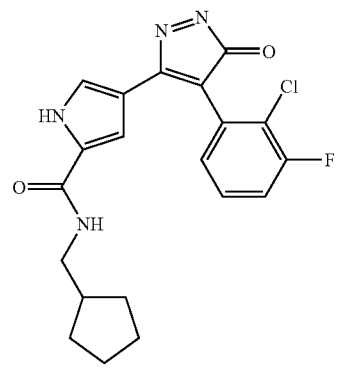
I-32
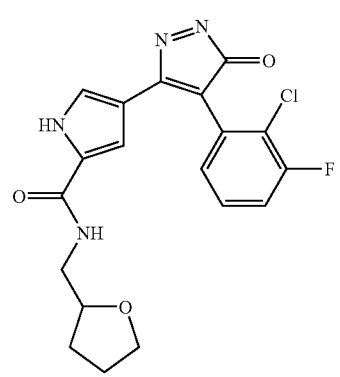

TABLE 1-continued
Examples of Compounds of Formula I:
I-33
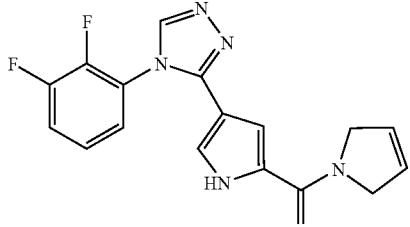
I-34
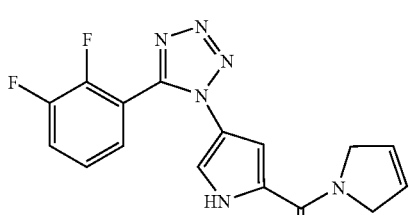
I-35
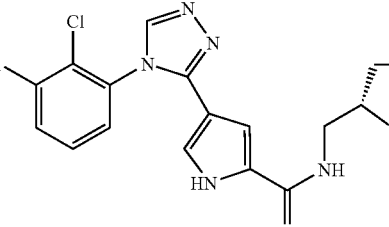
I-36
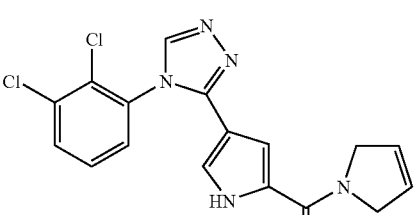
TABLE 1-continued
Examples of Compounds of Formula I:
I-37
I-38
I-39
I-40
I-41
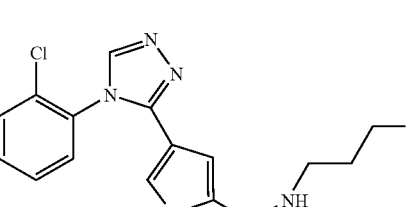

TABLE 1-continued
Examples of Compounds of Formula I:
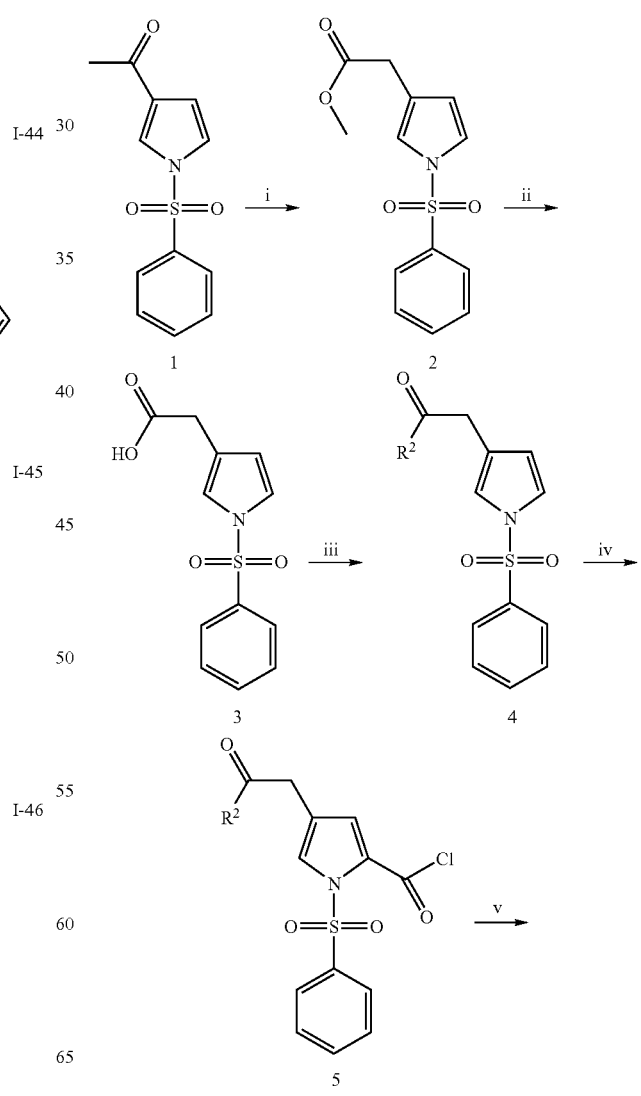
4. General Synthetic Methodology:
The compounds of this invention may be prepared in general by methods known to those skilled in the art for analogous compounds, as illustrated by the general scheme below, and the preparative examples that follow.

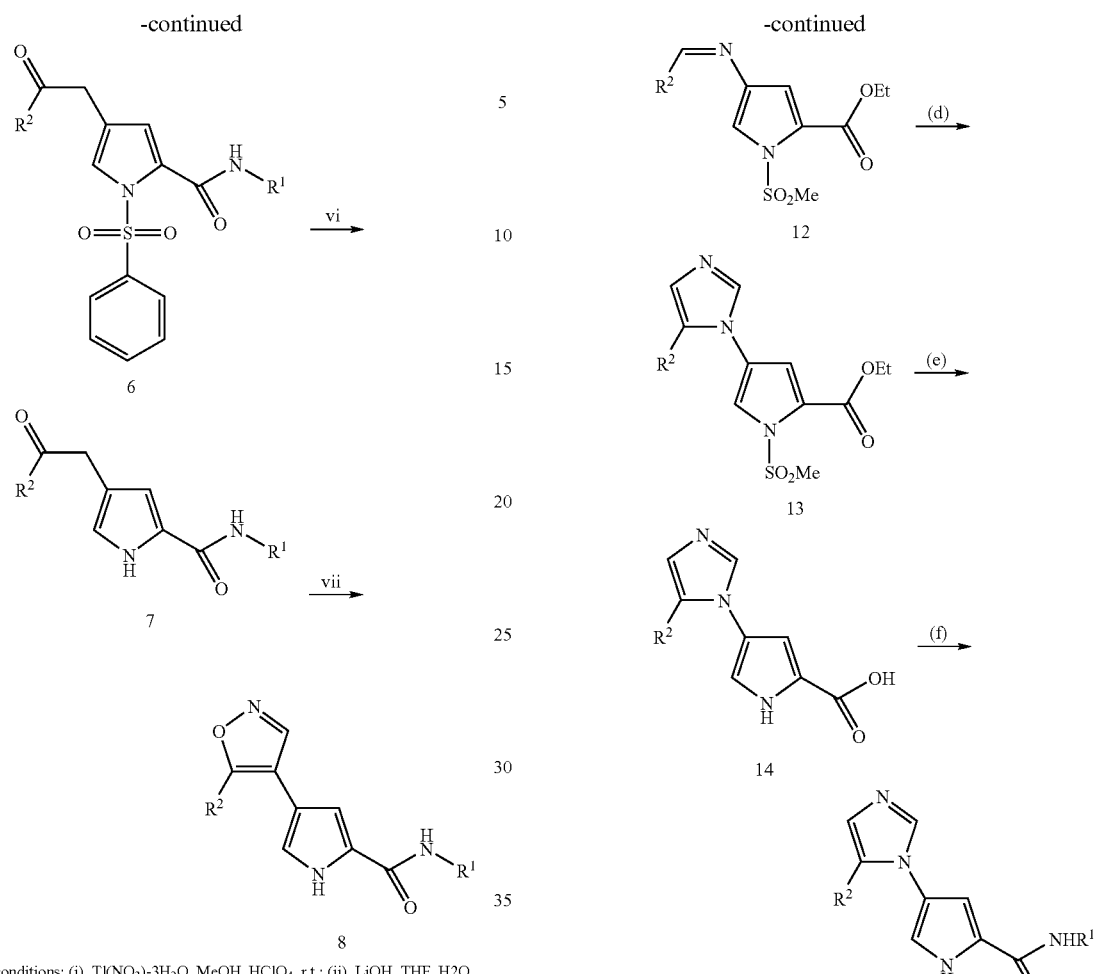

Reagents and conditions: (i). Tl(NO₃)-3H₂O, MeOH, HClO₄, r.t.; (ii). LiOH, THF, H2O, r.t.; (iii). a. LiN(TMS)₂, THF, -78° C. to 0° C.; b. R²CO₂Me; c. 2N HCl; (iv). (COCl)₂, AlCl₃, DCE; (v). R¹NH₂, CH₂Cl₂, r.t.; (vi). 6N NaOH; vii: a. Bredreck's reagent, THF, 60° C.; b. H₂NOH HCl, EtOH, reflux.

Scheme I above shows a general synthetic route for preparing compounds of the present invention when Ring A is isoxazolyl.

Reagents and conditions: (a). Me₂SO₂Cl, NaH, THF, r.t.; (b). H₂, Pd/C, EtOH, 50 psi; (c). TsOH, benzene, R²C(O)H; (d). Tos-MIC, K2CO3, MeOH, DME; (e). LiOH, THF, water; (f). R¹NH₂, CDI, DMAc.

Scheme II above shows a general synthetic route for preparing compounds of the present invention when Ring A is imidazolyl ring g.

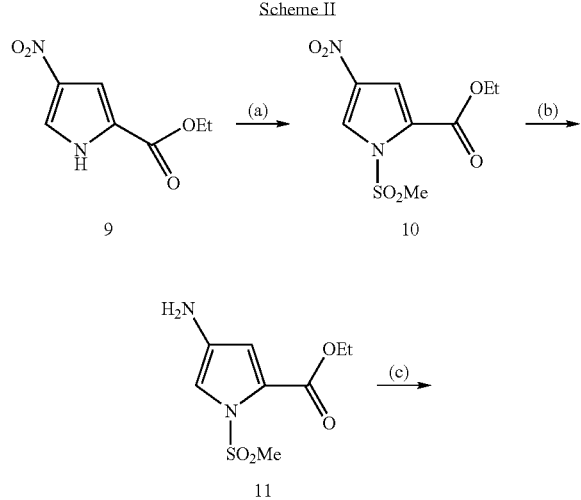

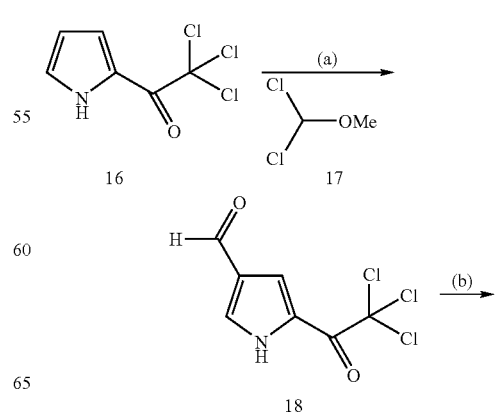

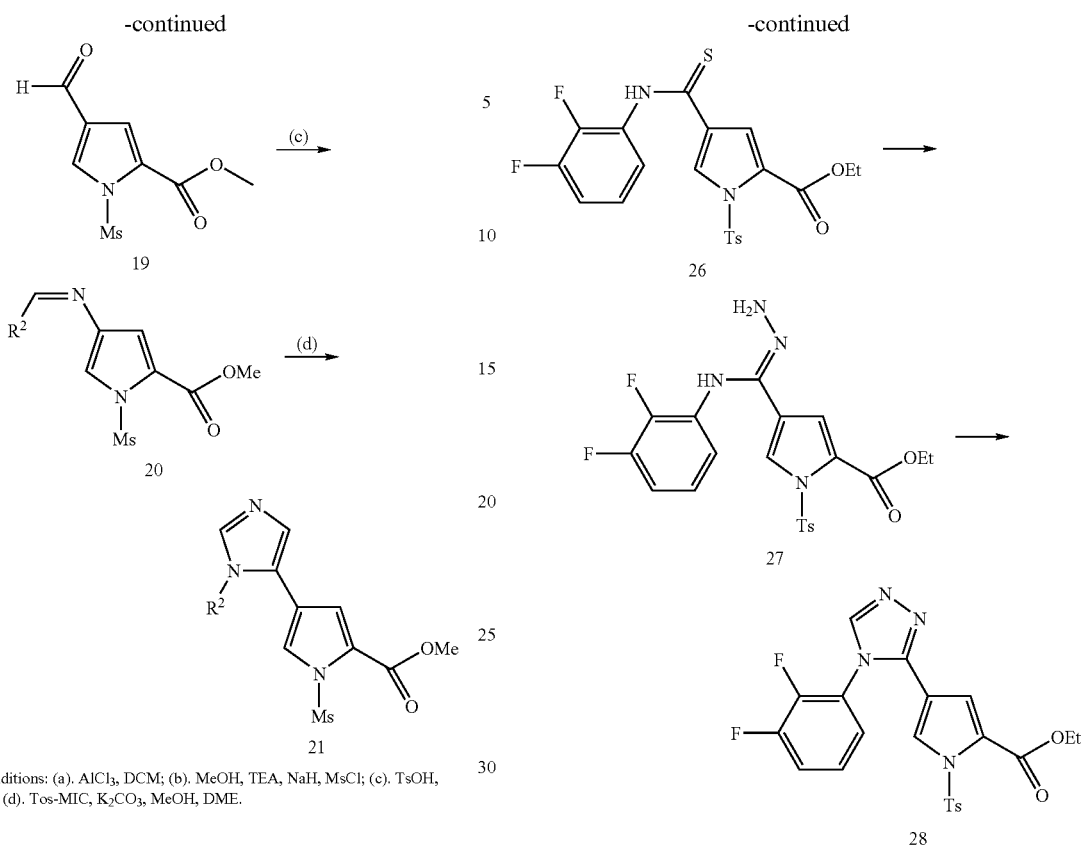

Reagents and conditions: (a). AlCl₃, DCM; (b). MeOH, TEA, NaH, MsCl; (c). TsOH, benzene, R²NH₂; (d). Tos-MIC, K₂CO₃, MeOH, DME.

Scheme III above shows a general synthetic route for preparing compounds of the present invention when Ring A is imidazolyl ring a.

Scheme IV above shows a general synthetic route for preparing compounds of the present invention when Ring A is triazolyl ring b. Compound 28 is then saponified to the carboxylate by the methods described above. The resulting carboxylate is coupled with a variety of groups, using methods known to one of ordinary skill in the art, to form a variety of compounds of the present invention.

Scheme IV

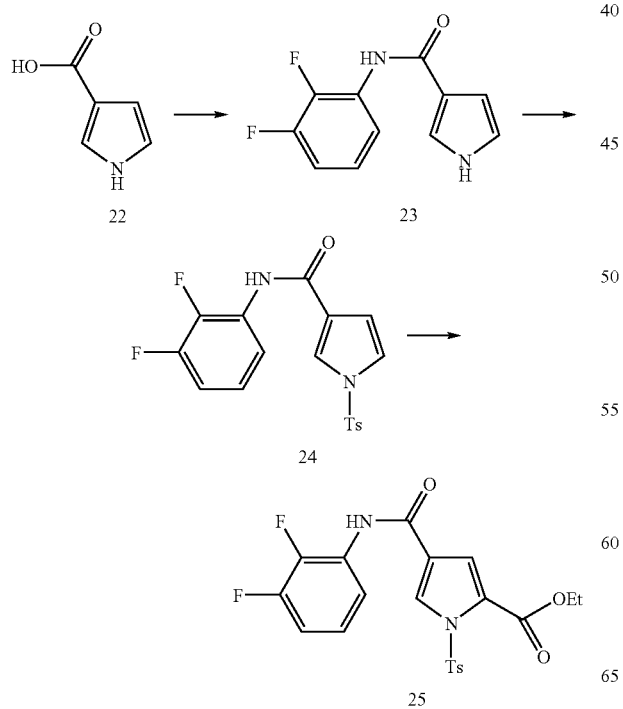

Scheme V

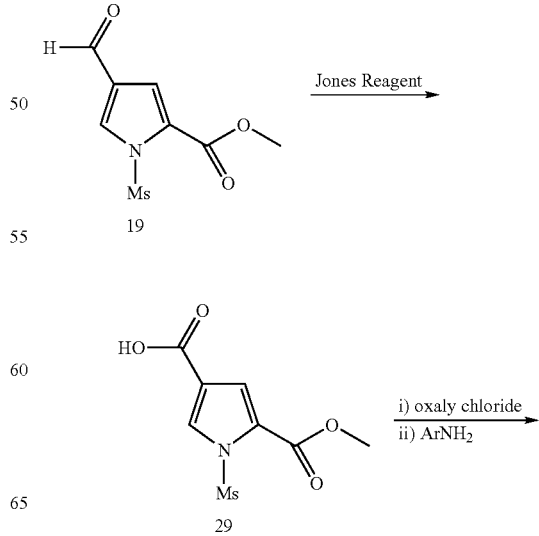

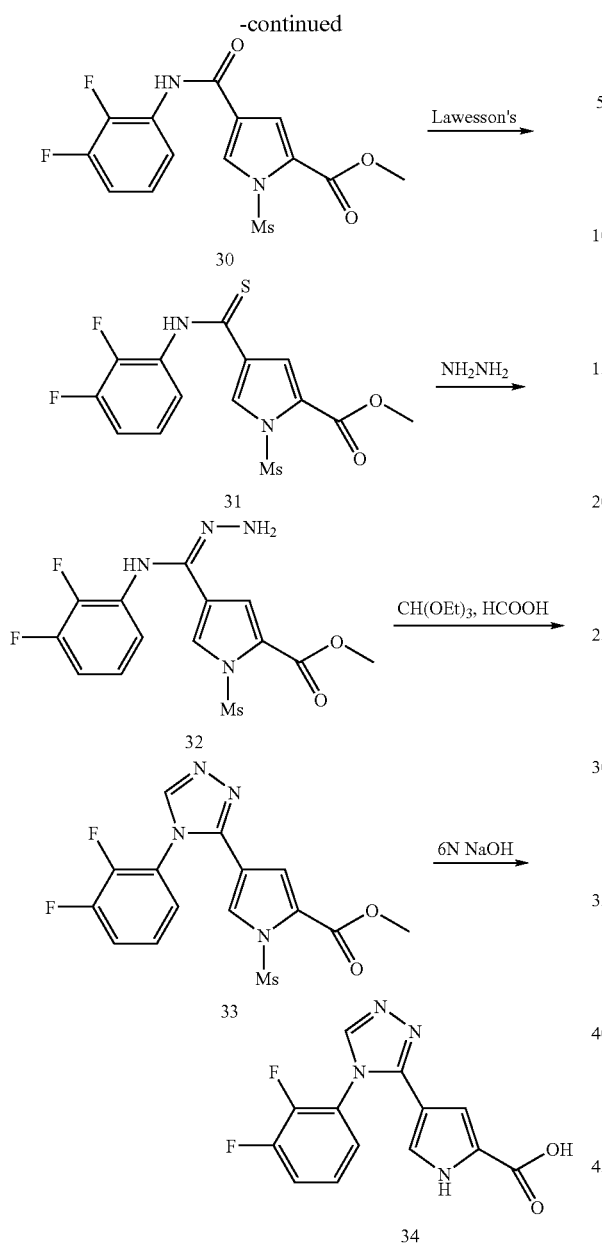

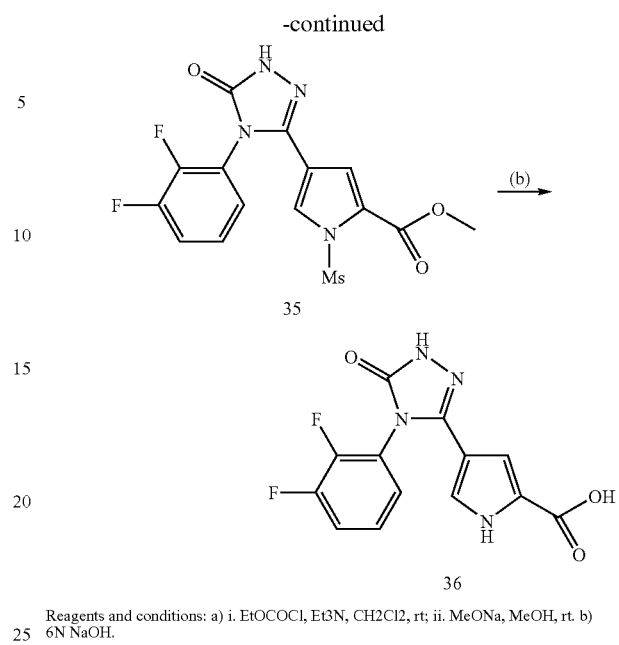

Reagents and conditions: a) i. EtOCOCl, Et3N, CH2Cl2, rt; ii. MeONa, MeOH, rt. b) 6N NaOH.

Scheme VI above shows a general synthetic route for preparing compounds of the present invention when Ring A is triazolyl ring b, substituted with oxo. The carboxylate 36 is coupled with a variety of groups, using methods known to one of ordinary skill in the art, to form a variety of compounds of the present invention.

Scheme VII

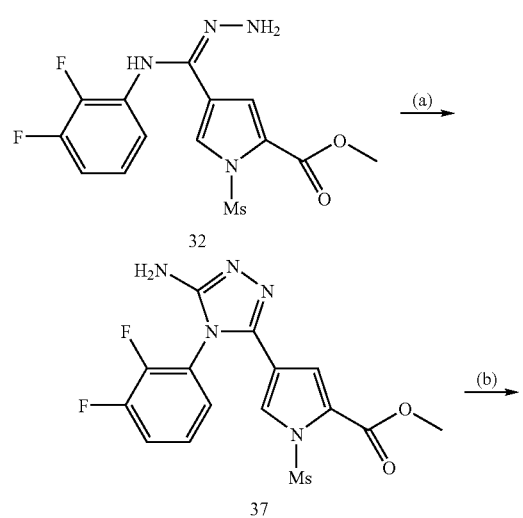

Scheme V above shows an alternate route for preparing compounds of the present invention when Ring A is triazolyl ring b. The carboxylate 34 is coupled with a variety of groups, using methods known to one of ordinary skill in the art, to form a variety of compounds of the present invention.

Scheme VI

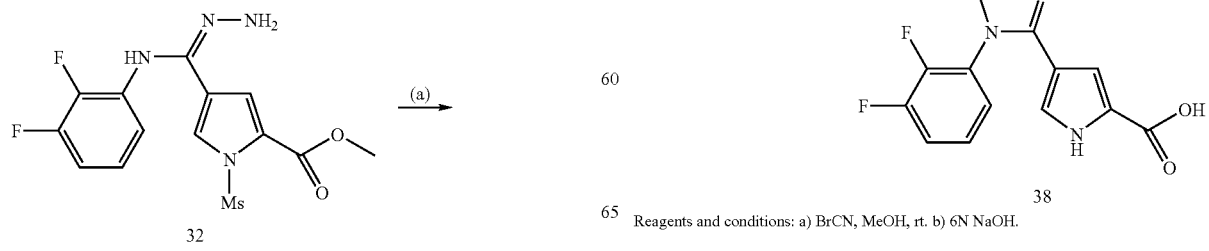

Reagents and conditions: a) BrCN, MeOH, rt. b) 6N NaOH.

Scheme VII above shows a general synthetic route for preparing compounds of the present invention when Ring A is triazolyl ring b, substituted with —NH$_2$. The carboxylate 38 is coupled with a variety of groups, using methods known to one of ordinary skill in the art, to form a variety of compounds of the present invention.

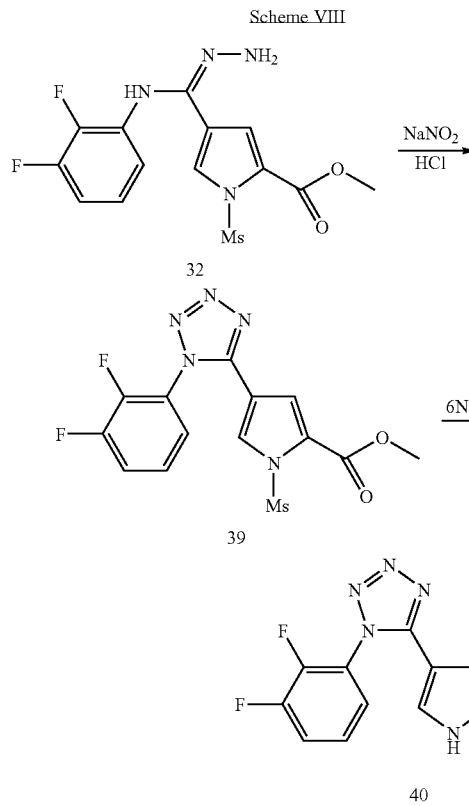

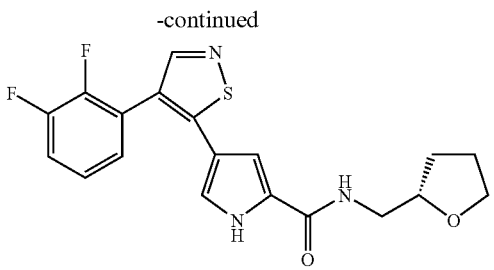

Reagents and conditions: a) 10% Pd/C, EtOH, H$_2$. b) P$_2$SO$_4$, toluene.

Scheme IX above shows a general synthetic route for preparing compounds of the present invention when Ring A is isothiazole ring m.

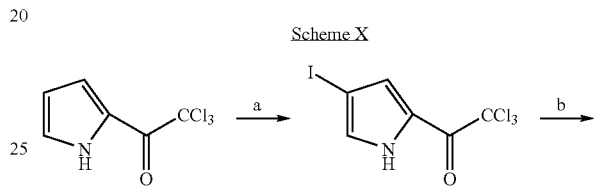

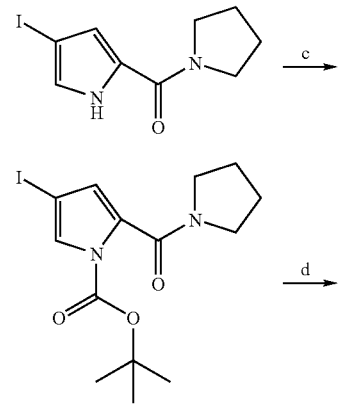

Scheme VIII above shows a general synthetic route for preparing compounds of the present invention when Ring A is tetrazole ring d. The carboxylate 40 is coupled with a variety of groups, using methods known to one of ordinary skill in the art, to form a variety of compounds of the present invention.

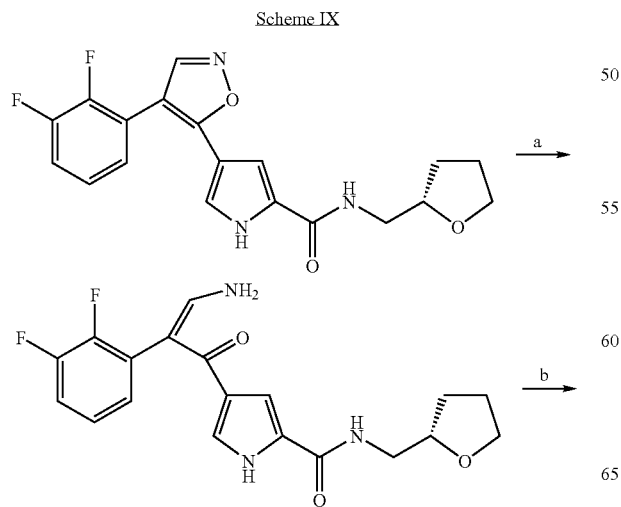

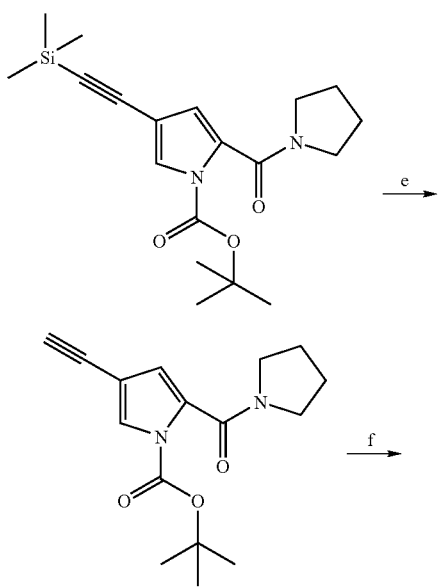

-continued

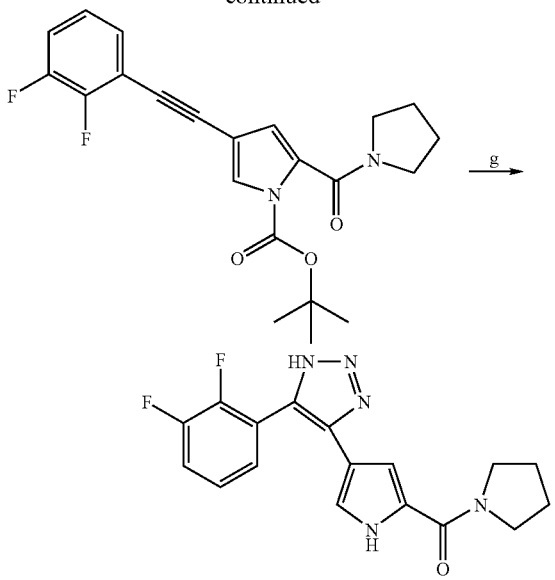

Reagents and conditions: a) ICl. b) pyrrolidine, MeCN. c) (Boc)₂O, CH₂Cl₂. d) Pd(PPh₃)₂Cl₂/CuI/NEt₃, TMS-acetylene. e) 1) K₂CO₃/MeOH, 2) (Boc)₂O, CH₂Cl₂. f) Pd(PPh₃)₂Cl₂/CuI/NEt₃, 1-bromo-2,3-difluorobenzene. g) TMSN₃

Scheme X above shows a general synthetic route for preparing compounds of the present invention when Ring A is triazolyl ring I.

Scheme XI

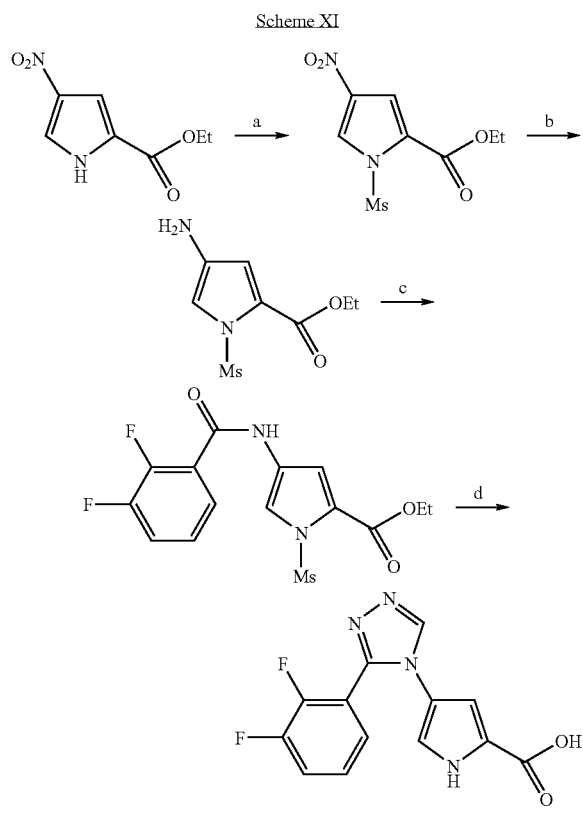

Reagents and conditions: a) NaH, Ms—Cl, THF. b) Pd/C, H2, EtOH/EtOAc. c) 2,3-difluorobenzoyl chloride, TEA, CH₂Cl₂ d) 6N NaOH Scheme XI above shows a general synthetic route for preparing compounds of the present invention when is Ring A is triazolyl ring J. The carboxylate is coupled with a variety of groups, using methods known to one of ordinary skill in the art, to form a variety of compounds of the present invention.

Accordingly, other embodiments of this invention provide processes for preparing compounds of formula I according to the general methods depicted in Schemes I-XI. It should be understood that specific depicted reagents and conditions could be modified in processes of this invention. In specific embodiments, the reagents and conditions are as depicted in Schemes I-XI.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration:

Pharmaceutically Acceptable Compositions

As discussed above, the present invention provides compounds that are inhibitors of protein kinases, and thus the present compounds are useful for the treatment of diseases, disorders, and conditions including, but not limited to cancer and other proliferative disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of c-Met protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer or other proliferative disorders is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a cancer or other proliferative disorder. The compounds and compositions, according to the method of the present invention, may be administered using any amount and any route of administration effective for treating or lessening the severity of a cancer or other proliferative disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of c-Met, and thus, without wishing to be bound by any particular theory, the compounds and compositions are particularly useful for treating or lessening the severity of a disease, condition, or disorder where activation of c-Met is implicated in the disease, condition, or disorder. When activation of c-Met is implicated in a particular disease, condition, or disorder, the disease, condition, or disorder may also be referred to as a "c-Met-mediated disease, disorder, or condition" or disease symptom. Accordingly, in another aspect, the present invention provides a method for treating or lessening the severity of a disease, condition, or disorder where activation of c-Met is implicated in the disease state.

The activity of a compound utilized in this invention as an inhibitor of c-Met, may be assayed in vitro, in vivo or in a cell line. In vitro assays include assays that determine inhibition of either the phosphorylation activity or ATPase activity of activated c-Met. Alternate in vitro assays quantitate the ability of the inhibitor to bind to c-Met. Inhibitor binding may be measured by radiolabelling the inhibitor prior to binding, isolating the inhibitor/c-Met, complex and determining the amount of radiolabel bound. Alternatively, inhibitor binding may be determined by running a competition experiment where new inhibitors are incubated with c-Met bound to known radioligands.

The term "measurably inhibit", as used herein means a measurable change in c-Met activity between a sample comprising said composition and a c-Met kinase and an equivalent sample comprising c-Met kinase in the absence of said composition.

The term "cMET-mediated disease" or "cMET-mediated condition", as used herein, means any disease state or other deleterious condition in which cMET is known to play a role. The terms "cMET-mediated disease" or "cMET-mediated condition" also mean those diseases or conditions that are alleviated by treatment with a cMET inhibitor. Such conditions include, without limitation, renal, colon, breast, prostate, and lung cancer, atherosclerosis and lung fibrosis.

According to one embodiment, the present invention relates to a method of treating or lessening the severity of renal, colon, breast, prostate, or lung cancer, atherosclerosis or lung fibrosis in a patient in need thereof, comprising administering to said patient a compound of the present invention or composition thereof.

According to another embodiment, the present invention relates to a method of treating or lessening the severity of renal cancer in a patient in need thereof, comprising administering to said patient a compound of the present invention or composition thereof.

Another aspect of the present invention relates to a method of inhibiting tumor metastasis in a patient in need thereof, comprising administering to said patient a compound of the present invention or composition thereof.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see the website for the U.S. National Cancer Institute. For a list of the FDA-approved oncology drugs see the website for the U.S. Food and Drug Administration and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting c-Met activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of c-Met kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, the term "$R_t$(min)" refers to the HPLC retention time, in minutes, associated with the compound. Unless otherwise indicated, the HPLC method utilized to obtain the reported retention time is as follows:
Column: XTerra C8 column, 4.6×150 mm
Gradient: 0-100% acetonitrile+methanol 60:40 (20 mM Tris phosphate)
Flow rate: 1.51 mL/minute
Detection: 225 nm.

EXAMPLES

Example 1

1-Methanesulfonyl-4-nitro-1H-pyrrole-2-carboxylic acid ethyl ester: To a solution of 4-nitro-1H-pyrrole-2-carboxylic acid ethyl ester (2.0 g, 10.86 mmol) in anhydrous THF (54 mL) was added NaH (650 mg, 60% dispersion, 16.25 mmol) at room temperature. The suspension was stirred at room temperature for 30 minutes before the addition of methanesulfonyl chloride (1.87 g, 16.32 mmol). The reaction mixture was stirred at room temperature over night. Water was carefully added to the reaction solution, and the resulting mixture was extracted with EtOAc (3×50 mL). The combined organic layers were washed with aqueous $NaHCO_3$ solution and brine, dried over $MgSO4$, filtered, and evaporated under reduced pressure to give a white solid (2.4 g, 84%). The crude product was used directly without purification. $^1$H NMR (500 MHz, DMSO-d6) δ8.36 (s, 1H), 7.60 (s, 1H), 4.33 (q, 2H), 4.02 (s, 3H), 2.51 (DMSO), 1.35 (t, 3H) ppm. MS (ES−): m/e=183.1 (M−Ms); LC/Method A/3.64 min.

Example 2

4-Amino-1-methanesulfonyl-1H-pyrrole-2-carboxylic acid ethyl ester: To a solution of 1-methanesulfonyl-4-nitro-1H-pyrrole-2-carboxylic acid ethyl ester (2.4 g, 9.15 mmol) in ethanol (30 mL) was added Pd/C (10%) (120 mg) under nitrogen atmosphere. The reaction flask was charged with hydrogen at 50 psi for 2 hours. The catalyst was removed by filtration through celite. The solvent was evaporated under reduced pressure to afford a sticky syrup that was purified by flash column eluting with 50% EtOAc in hexanes to give the product as sticky oil (2.1 g, 99%). MS (ES+): m/e=233.1 (M+H); LC/Method A/2.36 min.

Example 3

4-[(2,3-Difluoro-benzylidene)-amino]-1-methanesulfonyl-1H-pyrrole-2-carboxylic acid ethyl ester: To a solution of 4-amino-1-methanesulfonyl-1H-pyrrole-2-carboxylic acid ethyl ester (2.1 g, 9.04 mmol) in anhydrous benzene (100 mL) was added 2,3-difluoro-benzaldehyde (1.29 g, 9.08 mmol) and catalytic amount of TsOH. The reaction mixture was heated under reflux in the presence of Dean-Stark trap for 24 hours. The solvent was then removed by evaporation and the residue was dried on the high vacuum pump for 16 hours for the next step use (2.9 g crude product). $^1$H NMR (500 MHz, DMSO-d6) δ8.99 (s, 1H), 7.85 (t, 1H), 7.75 (s, 1H), 7.58 (m, 2H), 7.32 (m, 1H), 4.32 (q, 2H), 3.90 (s, 3H), 2.51 (DMSO), 1.35 (t, 3H) ppm.

Example 4

4-[5-(2,3-Difluoro-phenyl)-imidazol-1-yl]-1H-pyrrole-2-carboxylic acid: To a solution of 4-[(2,3-difluoro-benzylidene)-amino]-1-methanesulfonyl-1H-pyrrole-2-carboxylic acid ethyl ester (500 mg, 1.40 mmol) in co-solvents of MeOH (10 mL) and DME (5 mL) was added TosMIC (410 mg, 2.10 mmol) and $K_2CO_3$ (390 mg, 2,82 mmol). The reaction mixture was heated under reflux for 2 hours and the solvents were removed by evaporation. The residue was treated with LiOH in $THF/H_2O$ at room temperature for 14 hours. After removal of the solvents by evaporation, the residue was acidified by 2N HCl solution. The crude product was then purified by HPLC to afford 50 mg desired product (12%). MS (ES–): m/e=288.0 (M–H); LC/Method A/2.45 min.

Example 5

4-[5-(2,3-Difluoro-phenyl)-imidazol-1-yl]-1H-pyrrole-2-carboxylic acid (S-tetrahydro-furan-2-ylmethyl)-amide (I-10): To a solution of 4-[5-(2,3-difluoro-phenyl)-imidazol-1-yl]-1H-pyrrole-2-carboxylic acid (16 mg, 0.055 mmol) in anhydrous DMAc (1 mL) was added carbonyldiimidazole (9.0 mg, 0.055 mmol). The solution was stirred at room temperature for 1.5 hours before the addition of S-(tetrahydro-furan-2-yl)-methylamine (6 mg, 0.059 mmol). The reaction mixture was stirred at room temperature for 14 hours and then purified by HPLC to afford 11 mg of pure product as an off-white solid (53% yield). $^1$H NMR (500 MHz, DMSO-d6) δ12.01 (s, 1H), 8.99 (s, 1H), 8.23 (t, 1H), 7.88 (s, 1H), 7.56 (m, 1H), 7.30 (m, 1H), 7.16 (m, 2H), 6.83 (s, 1H), 3.91 (m, 1H), 3.75 (q, 1H), 3.62 (q, 1H), 3.27 (t, 2H), 1.88 (m, 1H), 1.80 (m, 2H), 1.52 (m, 1H) ppm. MS (ES–): m/e=371.1 (M–H); LC/Method A/2.65 min.

Example 6

4-[3-(2,3-Difluoro-phenyl)-3H-imidazol-4-yl]-1H-pyrrole-2-carboxylic acid (tetrahydro-furan-2-ylmethyl)-amide (I-16): The title compound was prepared by methods substantially similar to those used for the preparation of I-10, as described by Examples 1-5 above. The compound was purified by HPLC to afford 12 mg of pure product as a white solid (27% yield). $^1$H NMR (500 MHz, DMSO-d6) δ11.88 (s, 1H), 9.22 (s, 1H), 8.15 (t, 1H), 7.85 (s, 1H), 7.82 (q, 1H), 7.56 (t, 1H), 7.50 (q, 1H), 6.78 (s, 1H), 6.68 (s, 1H), 3.90 (m, 1H), 3.75 (q, 1H), 3.62 (q, 1H), 3.23 (t, 2H), 1.82 (m, 3H), 1.50 (m, 1H) ppm. MS (ES–): m/e=371.1 (M–H); LC/Method A/2.58 min.

Example 7

(1-Benzenesulfonyl-1H-pyrrol-3-yl)-acetic acid methyl ester: A mixture of 1-(1-benzenesulfonyl-1H-pyrrol-3-yl)-ethanone (5.0 g, 20.06 mmol), TTN (9.8 g, 22.05 mmol) and HClO$_4$ (1 mL) in MeOH was stirred at room temperature for 24 hours and filtered. The filtrate was concentrated at reduced pressure, diluted with ether, and filtered again. The filtrate was washed with water and then 10% of aqueous NaHCO$_3$ solution. The ether layer was dried over MgSO$_4$, filtered, and evaporated. The crude product was purified by flash column eluting with 20% of EtOAc in hexanes to give the desired product as an oil (3.64 g, 65%). $^1$H NMR (500 MHz, CDCl$_3$) δ7.90 (d, 2H), 7.65 (t, 1H), 7.55 (t, 2H), 7.12 (m, 2H), 6.30 (m, 1H), 3.71 (s, 3H), 3.48 (s, 2H) ppm. MS (ES+): m/e=280.1 (M+H); LC/Method A/3.58 min.

Example 8

(1-Benzenesulfonyl-1H-pyrrol-3-yl)-acetic acid: To a solution of (1-benzenesulfonyl-1H-pyrrol-3-yl)-acetic acid methyl ester (1.4 g, 5.01 mmol) in co-solvents of THF and water (1:1, 10 mL) was added LiOH hydrate (0.84 g, 20 mmol). The mixture was stirred at room temperature for 45 minutes and diluted with 50 mL of water. The resulting aqueous solution was washed once with EtOAc, acidified with 6N HCl, and extracted with EtOAc. The combined organic layers were dried over MgSO4 and concentrated to a sticky yellow oil (1.33 g, 100%). The crude product was used directly. MS (ES+): m/e=266.1 (M+H); LC/Method A/3.08 min.

Example 9

2-(1-Benzenesulfonyl-1H-pyrrol-3-yl)-1-(2,3-difluoro-phenyl)-ethanone: To a solution of (1-benzenesulfonyl-1H-pyrrol-3-yl)-acetic acid (1.3 g, 4.90 mmol) in THF was added LiN(TMS)$_2$ (12 mL, 1.0M in THF, 12 mmol) at –78° C. The resulting solution was stirred at this temperature for 1 hour and 0° C. for 1 hour and then was cooled to –78° C. again. To this solution was added 2,3-difluoro-benzoic acid methyl ester (1.1 g, 6.40 mmol) and the reaction was stirred at room temperature for 14 hours. The solution was poured into 2N HCl and extracted with EtOAc. The combined organic layers were dried over MgSO$_4$, filtered, and evaporated. The crude product was purified by flash column eluting with 20% of EtOAc in hexanes to afford the title compound as a yellow oil (1.1 g, 58%). $^1$H NMR (500 MHz, CDCl$_3$) δ7.77 (d, 2H), 7.50 (m, 2H), 7.42 (t, 2H), 7.28 (m, 1H), 7.05 (m, 3H), 6.18 (m, 1H), 3.98 (s, 2H) ppm. MS (ES+): m/e=362.1 (M+H); LC/Method A/3.98 min.

Example 10

1-Benzenesulfonyl-4-[2-(2,3-difluoro-phenyl)-2-oxo-ethyl]-1H-pyrrole-2-carboxylic acid (tetrahydro-furan-2-ylmethyl)-amide: To an ice-cooled suspension of AlCl$_3$ (184 mg, 1.38 mmol) in dry 1,2-dichloroethane (3 mL) was added oxalyl chloride (175 mg, 1.38 mmol). The resulting solution was stirred at 0° C. for 20 minutes, then added 2-(1-benzenesulfonyl-1H-pyrrol-3-yl)-1-(2,3-difluoro-phenyl)-ethanone (100 mg, 0.28 mmol). The mixture was stirred at room temperature for 60 minutes and then poured into ice-water. After stirring for 30 minutes, the aqueous solution was extracted with dichloromethane, the combined organic layers were dried over MgSO$_4$ and filtered. The solvents were removed by evaporation and the crude product was dried on the vacuum pump for 3 hours. To the resulting crude product was added dry dichloromethane (4 mL) and S-(tetrahydro-furan-2-yl)-methylamine (56 mg, 0.55 mmol). The solution was stirred at room temperature for 3 hours. The solvent was removed and the residue was purified by flash column eluting with 30-50% EtOAc in hexanes to afford a white solid (60 mg, 44% for two steps). MS (ES+): m/e=489.2 (M+H); LC/Method A/3.73 min.

Example 11

4-[2-(2,3-Difluoro-phenyl)-2-oxo-ethyl]-1H-pyrrole-2-carboxylic acid (S-tetrahydro-furan-2-ylmethyl)-amide: To a solution of 1-benzenesulfonyl-4-[2-(2,3-difluoro-phenyl)-2-oxo-ethyl]-1H-pyrrole-2-carboxylic acid (tetrahydro-furan-2-ylmethyl)-amide (60 mg, 0.12 mmol) in MeOH (1 mL) was added 6N NaOH solution (1 mL). The mixture was heated at 60° C. for 30 minutes and cooled. The solvent was evaporated under reduced pressure and the residue was acidified by 2N HCl. The resulting acidic aqueous solution was then extracted with EtOAc and the combined organic layers were dried over MgSO$_4$, filtered, and evaporated. The crude product was dried on the vacuum pump for 10 hours for the next step (40 mg, 93%). MS (ES+): m/e=349.2 (M+H); LC/Method A/3.19 min.

Example 12

4-[5-(2,3-Difluoro-phenyl)-isoxazol-4-yl]-1H-pyrrole-2-carboxylic acid (S-tetrahydro-furan-2-ylmethyl)-amide (I-4): To a solution of crude 4-[2-(2,3-difluoro-phenyl)-2-oxo-ethyl]-1H-pyrrole-2-carboxylic acid (S-tetrahydro-furan-2-ylmethyl)-amide (40 mg, 0.11 mmol) in THF was added Bredreck's reagent (60 mg, 0.34 mmol), the resulting solution was heated at 60° C. for 3 hours. The solvent was removed and EtOH was added to the residue. After stirring at room temperature for 5 minutes, $NH_2OH$ HCl (38 mg, 0.55 mmol) was added and the mixture was heated at reflux for 8 hours. The solvent was removed and the residue was purified by HPLC to afford the pure desired product (6 mg, 14%) as a golden yellow solid. $^1$HNMR (500 MHz, $CDCl_3$) δ11.68 (s, 1H), 8.96 (s, 1H), 8.05 (t, 1H), 7.68 (dd, 1H), 7.49 (t, 1H), 7.42 (dd, 1H), 7.10 (s, 1H), 6.78 (s, 1H), 3.95 (m, 1H), 3.77 (q, 1H), 3.62 (q, 1H), 3.25 (t, 2H), 1.80 (m, 3H), 1.52 (m, 1H) ppm. MS (ES+): m/e=374.2 (M+H); LC/Method A/3.33 min.

Example 13

{4-[5-(2,3-Difluoro-phenyl)-isoxazol-4-yl]-1H-pyrrol-2-yl}-pyrrolidin-1-yl-methanone (I-6): The title compound was prepared in a manner substantially similar to that used for the preparation of I-4, as described by Examples 7-12 above. The compound was purified by HPLC to afford 9 mg of pure product as a yellow solid (13% yield). $^1$H NMR (500 MHz, DMSO-d6) δ11.65 (s, 1H), 9.07 (s, 1H), 7.70 (dd, 1H), 7.50 (dd, 1H), 7.42 (dd, 1H), 7.07 (s, 1H), 6.64 (s, 1H), 3.55 (br, 2H), 3.45 (br, 2H), 1.92 (br, 2H), 1.81 (br, 2H) ppm. MS (ES+): m/e=344.2 (M+H); LC/Method A/3.48 min.

Example 14

5-Trichloroacetyl-1H-pyrrole-3-carbaldehyde: A solution of 2,2,2-trichloro-1-(1H-pyrrol-2-yl)-ethanone (5.0 g, 23.53 mmol) and $AlCl_3$ (3.8 g, 28.50 mmol) in co-solvents of EDC (20 mL) and $MeNO_2$ (20 mL) was cooled to –10° C. A solution of dichloro-methoxy-methane (3.25 g, 28.27 mmol) in EDC (5 mL) was added fairly rapidly and the mix was then stirred at –10° C. to room temperature for overnight. It was poured over crushed ice, the layer were separated, and the aqueous phase was extracted with $CH_2Cl_2$. The combined organic layers were washed, dried over MgSO4, and concentrated, yielding a slightly reddish solid (3.6 g, 64%). $^1$H NMR (500 MHz, CDCl3) δ10.10 (s, 1H), 10.06 (br, 1H), 7.96 (m, 2H) ppm. MS (ES–): m/e=238 (M–H); LC/Method A/3.15 min.

Example 15

4-Formyl-1-methanesulfonyl-1H-pyrrole-2-carboxylic acid methyl ester: To a solution of 5-trichloroacetyl-1H-pyrrole-3-carbaldehyde (3.6 g, 14.97 mmol) in MeOH (60 mL) was added triethylamine (2 mL). The reaction mixture was stirred at room temperature for 3 hours. The solvent was removed and the residue was dried on the vacuum pump for 6 hours. This crude product was then dissolved in 60 mL of anhydrous THF. To the resulting solution was added NaH (720 mg, 18 mmol) at room temperature. The suspension was then stirred at room temperature for 1 hour before addition of MsCl (2.6 g, 22.70 mmol). The mixture was left at room temperature overnight and then poured into 2N HCl solution (100 mL). The aqueous solution was extracted with EtOAc (3×60 mL), the combined organic layers were dried over $MgSO_4$, the solvent was removed by evaporation, and the residue was purified by flash column eluting with 30% EtOAc/hexanes to afford the title compound as a white solid (2.85 g, 82%). $^1$H NMR (500 MHz, DMSO-d6) δ9.88 (s, 1H), 8.40 (s, 1H), 7.40 (s, 1H), 3.96 (s, 3H), 3.85 (s, 3H) ppm. MS (ES+): m/e=232.1 (M+H); LC/Method A/2.61 min.

Example 16

1-Methanesulfonyl-1H-pyrrole-2,4-dicarboxylic acid 2-methyl ester: The Jones reagent was made up in 1.00-mol batches by dissolving 100 g of $CrO_3$ in a minimum of distilled water. Sulfuric acid (87 mL) was added and more water (200 mL total) was then added to effect solution of precipitated $CrO_3$. The final volume was 350 mL (2.86 M with respect to $CrO_3$). To a solution of 4-formyl-1-methanesulfonyl-1H-pyrrole-2-carboxylic acid methyl ester (700 mg, 3.03 mmol) in acetone (5 mL) was added the Jones reagent at 10° C. dropwise until a persistent orange color was observed. The reaction mixture was stirred for additional 20 minutes, and then the orange color was removed by the addition of isopropyl alcohol. After dilution with water (20 mL) the solution was extracted with $CHCl_3$ (3×30 mL). The combined organic layers were washed once by water and then extracted to aqueous $NaHCO_3$ solution (60 mL). The $NaHCO_3$ solution was acidified by concentrated HCl to pH 2 and the resulting white precipitate was collected by filtration and washed with cold water. The crude product was dried on the oil pump for the next step without further purification (600 mg, 80%). $^1$H NMR (500 MHz, DMSO-d6) δ12.87 (s, 1H), 7.91 (s, 1H), 7.30 (s, 1H), 3.93 (s, 3H), 3.84 (s, 3H) ppm. MS (ES+): m/e=248.1 (M+H); LC/Method A/2.38 min.

Example 17

4-(2,3-Difluoro-phenylcarbamoyl)-1-methanesulfonyl-1H-pyrrole-2-carboxylic acid methyl ester: To a solution of 1-methanesulfonyl-1H-pyrrole-2,4-dicarboxylic acid 2-methyl ester (290 mg, 1.17 mmol) in dry $CH_2Cl_2$ (5 mL) and DMF (2 drops) was added oxalyl chloride (220 mg, 1.73 mmol) at room temperature. The mixture was stirred for 1 hour and evaporated. The residue was dried on the vacuum pump for 4 hours and then dissolved in dry $CH_2Cl_2$ (5 mL). To this solution was added 2,3-difluoro-phenylamine (300 mg, 2.32 mmol) and triethylamine (240 mg, 2.37 mmol). The reaction mixture was stirred for another 1 hour then poured into 2N HCl solution. The aqueous solution was extracted with EtOAc and the combined organic layers were dried over $MgSO_4$. After removal of solvent by evaporation, the residue was purified by flash column eluting with 20% EtOAc/hexanes to afford the title compound as a yellow solid (410 mg, 98%). MS (ES+): m/e=359.1 (M+H); LC/Method A/3.31 min.

Example 18

4-(2,3-Difluoro-phenylthiocarbamoyl)-1-methanesulfonyl-1H-pyrrole-2-carboxylic acid methyl ester: To a solution of 4-(2,3-difluoro-phenylcarbamoyl)-1-methanesulfonyl-1H-pyrrole-2-carboxylic acid methyl ester (410 mg, 1.14 mmol) in dry toluene (10 mL) was added Lawesson's reagent (320 mg, 0.79 mmol). The suspension was heated at reflux for 2 hours. The solvent was removed by evaporation and the residue was purified by flash column eluting with 30% of EtOAc/hexanes to afford the title compound as a yellow solid (425 mg, 99%). MS (ES+): m/e=375.1 (M+H); LC/Method A/3.61 min.

Example 19

4-[N-(2,3-Difluoro-phenyl)-N'-amino-carbamimidoyl]-1-methanesulfonyl-1H-pyrrole-2-carboxylic acid methyl ester: To a solution of 4-(2,3-difluoro-phenylthiocarbamoyl)-1-methanesulfonyl-1H-pyrrole-2-carboxylic acid methyl ester (420 mg, 1.12 mmol) in $CH_2Cl_2$ (5 mL) and EtOH (5 mL) was added $NH_2NH_2$ (50 mg, 1.56 mmol) at room temperature. The mixture was stirred for 3 hours and the solvents were removed by evaporation under reduced pressure. The crude yellow solid product (410 mg, 98%) was dried on the pump for direct use. MS (ES+): m/e=373.1 (M+H); LC/Method A/2.70 min.

Example 20

4-[4-(2,3-Difluoro-phenyl)-4H-[1,2,4]triazol-3-yl]-1H-pyrrole-2-carboxylic acid: A mixture of 4-[N-(2,3-difluoro-phenyl)-N'-amino-carbamimidoyl]-1-methanesulfonyl-1H-pyrrole-2-carboxylic acid methyl ester (200 mg, 0.54 mmol), $CH(OEt)_3$ (4 mL), and HCOOH (0.8 mL) was stirred at room temperature for 2 hours and poured into 50 mL of aqueous $NaHCO_3$ solution. The aqueous mixture was extracted with EtOAc and the combined organic layers were dried over $Na_2SO_4$, filtered, and evaporated. The crude material was used for the next step without further purification. This crude product was dissolved in MeOH (5 mL) then 6N NaOH aqeous solution was added (1 mL) and the mixture was heated at 50° C. for 3 hours. The solvent was evaporated and the residue was acidified with 6N HCl to pH 3. The white precipitate was collected by filtration and washed with water. The crude product (150 mg, 96%) was dried on the pump for the next reaction. $^1$H NMR (500 MHz, DMSO-d6) δ12.61 (s, br, 1H), 12.20 (s, 1H), 8.78 (s, 1H), 7.75 (m, 1H), 7.55 (m, 1H), 7.47 (m, 1H), 6.96 (s, 1H), 6.58 (s, 1H) ppm. MS (ES+): m/e=291.1 (M+H); LC/Method A/2.46 min.

Example 21

4-[4-(2,3-Difluoro-phenyl)-4H-[1,2,4]triazol-3-yl]-1H-pyrrole-2-carboxylic acid (S-tetrahydro-furan-2-ylmethyl)-amide (I-20): To a solution of 4-[4-(2,3-difluoro-phenyl)-4H-[1,2,4]triazol-3-yl]-1H-pyrrole-2-carboxylic acid (50 mg, 0.17 mmol) in DMA (1 mL) was added CDI (31 mg, 0.19 mmol). The solution was stirred at room temperature for 30 minutes then S-(tetrahydro-furan-2-yl)-methylamine (35 mg, 0.34 mmol) was added. The reaction mixture was stirred for another 60 minutes and purified by preparative HPLC (Gilson) to afford a white solid (30 mg, 47%). $^1$H NMR (500 MHz, DMSO-d6) δ11.87 (s, 1H), 8.84 (s, 1H), 8.25 (t, 1H), 7.75 (m, 1H), 7.48 (m, 2H), 7.00 (s, 1H), 6.70 (s, 1H), 3.94 (m, 1H), 3.75 (m, 1H), 3.61 (m, 1H), 2.23 (m, 2H), 1.82 (m, 3H), 1.55 (m, 1H) ppm. MS (ES+): m/e=374.2 (M+H); LC/Method A/2.66 min.

Example 22

(4-(4-(2,3-difluorophenyl)-4H-1,2,4-triazol-3-yl)-1H-pyrrol-2-yl)(2H-pyrrol-1(5H)-yl)methanone (I-37): The title compound was prepared in a manner substantially similar to that used for the preparation of I-20, as described by Examples 14-20 above to afford the title compound as a white solid (44 mg, 75%). $^1$H NMR (500 MHz, DMSO-d6) δ11.89 (s, 1H), 8.80 (s, 1H), 7.78 (m, 1H), 7.55 (m, 1H), 7.46 (m, 1H), 6.77 (s, 1H), 6.66 (s, 1H), 5.95 (d, 2H), 4.35 (s, 2H), 4.22 (s, 2H) ppm. MS (ES+): m/e=342.2 (M+H); LC/Method A/2.76 min.

Example 23

4-[4-(2,3-Difluoro-phenyl)-4H-[1,2,4]triazol-3-yl]-1H-pyrrole-2-carboxylic acid phenylamide (I-17): The title compound was prepared in a manner substantially similar to that used for the preparation of I-18 to afford the title compound as a white solid (18 mg, 29%). $^1$H NMR (500 MHz, DMSO-d6) δ12.00 (s, 1H), 9.95 (s, 1H), 8.80 (s, 1H), 7.75 (m, 1H), 7.71 (d, 2H), 7.54 (m, 1H), 7.47 (m, 1H), 7.37 (s, 1H), 7.33 (t, 2H), 7.06 (t, 1H), 6.64 (s, 1H) ppm. MS (ES+): m/e=366.2 (M+H); LC/Method A/3.06 min.

Example 24

4-[1-(2,3-Difluoro-phenyl)-1H-tetrazol-5-yl]-1-methanesulfonyl-1H-pyrrole-2-carboxylic acid methyl ester: To a solution of 4-[N-(2,3-difluoro-phenyl)-N'-amino-carbamimidoyl]-1-methanesulfonyl-1H-pyrrole-2-carboxylic acid methyl ester (250 mg, 0.67 mmol) in 2N HCl (10 mL) was added a solution of $NaNO_2$ (56 mg, 0.81 mmol) in water (2 mL) slowly at 0° C. The reaction mixture was stirred at this temperature for 5 minutes and then neutralized by addition of 6N NaOH. The resulting white precipitate was collected by filtration and washed with water. After drying on the vacuum pump for 6 hours, the crude product was obtained (250 mg, 97%) as white solid. $^1$H NMR (500 MHz, DMSO-d6) δ7.94 (q, 1H), 7.78 (t, 1H), 7.68 (s, 1H), 7.60 (q, 1H), 7.15 (s, 1H), 3.94 (s, 3H), 3.82 (s, 3H) ppm. MS (ES+): m/e=384.1 (M+H); LC/Method A/3.63 min.

Example 25

4-[1-(2,3-Difluoro-phenyl)-1H-tetrazol-5-yl]-1H-pyrrole-2-carboxylic acid (tetrahydro-furan-2-ylmethyl)-amide (I-24): Prepared by methods substantially similar as used for the preparation of I-18, except for the tetrazole formation step (shown above at Example 24) to afford the title compound as a white solid (35 mg, 64%). $^1$H NMR (500 MHz, DMSO-d6) δ12.20 (s, 1H), 8.35 (t, 1H), 7.89 (q, 1H), 7.70 (t, 1H), 7.55 (m, 1H), 7.10 (s, 1H), 6.95 (s, 1H), 3.92 (m, 1H), 3.78 (m, 1H), 3.62 (m, 1H), 3.25 (m, 2H), 1.85 (m, 3H), 1.55 (m, 1H) ppm. MS (ES+): m/e=375.2 (M+H); LC/Method A/3.03

Example 26

(4-(5-(2,3-difluorophenyl)-1H-tetrazol-1-yl)-1H-pyrrol-2-yl)(2H-pyrrol-1(5H)-yl)methanone (I-38): Prepared by methods substantially similar as used for the preparation of I-24 to afford the title compound as a white solid (37 mg, 63%). $^1$H NMR (500 MHz, DMSO-d6) δ12.24 (s, 1H), 7.90 (q, 1H), 7.75 (t, 1H), 7.57 (m, 1H), 7.02 (s, 1H), 6.78 (s, 1H), 5.96 (d, 2H), 4.38 (s, 2H), 4.26 (s, 2H) ppm. MS (ES+): m/e=343.2 (M+H); LC/Method A/3.13

Example 27

4-(4-(2,3-difluorophenyl)isothiazol-5-yl)-N-(((S)-tetrahydrofuran-2-yl)methyl)-1H-pyrrrole-2-carboxamide (I-46). 10% Palladium on carbon (0.2 g) was suspended in a degassed solution of compound 1(0.2 g, 0.54 mmol) in ethanol (10 mL) and then hydrogenated for 2 hr at room temperature. The solid was filtered and the filtrate was concentrated to afford enamino-ketone 2 (0.2 g).; Mass Spec FIA MS 376 (M+1). Compound 2 was dissolved in toluene (5 mL) and phosphorous pentasulfide (0.71, 1.6 mmol) and chloranil (0.13 g, 0.5 mmol) were added. The solution was heated at 120° C. for 15 min and cooled to room temperature. The solution was diluted with ethyl acetate (50 mL) and washed with brine and water. The organic phase was dried and concentrated to afford a brown residue which was purified by Biotage HPFC system (40-70% EtOAC/Hexane) to afford the title compound (12 mg, 6%). Mass Spec.; LC MS 390(M+1); $^1$H NMR(CDCl$_3$, 500 MHz) δ9.45(brS, 1H), 8.32(s, 1H), 6.95-7.16(m, 3H), 6.76(d, 1H), 6.43(s, 1H), 6.14(bt, 1H), 3.95(m, 1H), 3.80(dd, 1H), 3.70(dd, 1H), 3.59(m, 1H), 3.22-3.26(m, 1H), 1.80-1.97(m, 3H), 1.49-1.53 (m, 1H).

Example 28

(4-Iodo-1H-pyrrol-2-yl)(pyrrolidin-1-yl)methanone. Pyrrolidine (3 mL, 35.62 mmol) was added to a stirred solution of 4-iodo-2-(trichloroacetyl)pyrrole (10 g, 29.69 mmol) in acetonitrile (50 mL) at room temperature. The mixture was stirred at room temperature for 1 hr. The white precipitate was filtered and washed with acetonitrile (25 mL) to give title compound as a white solid (7.3 g, 86%).; Mass Spec FIA MS 291.

Example 29

4-Iodo-1-BOC-pyrrol-2-yl)(pyrrolidin-1-yl)methanone. Di-tert-butyl dicarbonate (5.2 g, 24.12 mmol) was added to a stirred solution of (4-Iodo-1H-pyrrol-2-yl)(pyrrolidin-1-yl)methanone (7 g, 24.12 mmol) and DMAP (0.1 g) in acetonitrile (50 mL) at room temperature. The solution was stirred at room temperature for 2 hr. The solvent was evaporated and the crude product was dissolved in ethyl acetate (50 mL). The organic layer was washed with brine and water. The solvent was removed under reduced pressure to afford the title compound as an oil (9 g, 93%).; Mass Spec FIA MS 401.

Example 30

(4-(2-(Trimethylsilyl)ethynyl)-1-BOC-pyrrol-2-yl)(pyrrolidin-1-yl)methanone. A mixture of 4-Iodo-1-BOC'-pyrrol-2-yl)(pyrrolidin-1-yl)methanone (9 g, 22.5 mmol), trimethylsilylacetylene (13.5 mL, 96 mmoL), PdCl$_2$PPh$_2$(1.6 g, 2.25 mmol) and CuI (0.85 g, 4.5 mmol) in trietylamine (50 mL) was stirred at room temperature for 2 hr. The solid was filtered and washed with ethyl acetate (100 mL). The filtrate was collected and washed with 2N HCl (3×100 mL), brine (100 mL) and water (100 mL). The organic layer was dried and concentrated under reduced pressure to afford title compound (7.2 g, 83%) as a viscous oil.

Example 31

(4-ethynyl)-1-H pyrrol-2-yl)(pyrrolidin-1-yl)methanone. Potassium carbonate (2.7 g, 20 mmol) was added to a solution of (4-(2-(Trimethyl-silyl)ethynyl)-1-BOC pyrrol-2-yl)(pyrrolidin-1-yl)methanone (7 g, 19.43 mmol) in methanol (50 mL). The solution was stirred at room temperature for 16 hr. The solid was filtered and the filtrate was concentrated to give title compound. (3.6 g, 100%).; Mass Spec FIA MS 189. $^1$H NMR (DMSO-d6, 500 MHz) δ11.8 (brs, 1H), 7.11(s,1H), 6.67(s,1H), 3.42-3.80(m,4H), 3.16(s,1H), 1.70-1.95(brm,4H).

Example 32

(4-ethynyl)-1-BOC pyrrol-2-yl)(pyrrolidin-1-yl)methanone. Di-tert-butyl dicarbonate (3.6 g, 19.14 mmol) was added to a stirred solution of (4-ethynyl)-1-H pyrrol-2-yl)(pyrrolidin-1-yl)methanone (7 g, 24.12 mmol) and DMAP (0.1 g) in acetonitrile (50 mL) at room temperature. The solution was stirred at RT for 2 hr. The solvent was evaporated and the crude was dissolved in ethyl acetate (50 mL). The organic layer was washed with brine and water. The solvent was removed under reduced pressure. The crude product was purified by Biotage HPFC system (20-40% EtOAC/Hexane) to afford title as a brown oil (4.1 g, 65%).; $^1$H NMR(CDCl$_3$, 500 MHz) 7.41(d,1H), 6.33(d,1H), 3.57 (t,2H), 3.28(t,2H), 2.94(s,1H), 1.86-1.95(m,4H), 1.53(s,9H).

Example 33

(4-(2-(2,3-difluorophenyl)ethynyl)-1-BOC-pyrrol-2-yl)(pyrrolidin-1-yl)methanone. A mixture of (4-ethynyl)-1-BOC-pyrrol-2-yl)(pyrrolidin-1-yl)methanone (4 g, 13.88 mmol), 2,3-difluoro-1-bromobenzene (4 g, 20.8 mmol), PdCl$_2$PPh$_2$(0.97 g, 1.38 mmol) and CuI (0.53 g, 2.76 mmol in trietylamine (40 mL) was stirred at room temperature for 4 hr. The solid was filtered and washed with ethyl acetate (100 mL). The filtrate was washed with 2N HCl (3×100 mL), brine (100 mL) and water (100 mL). The organic layer was dried and concentrated under reduced pressure. The crude product was purified by Biotage HPFC system (40-65% EtOAC/Hexane) to afford title as a dark brown oil (1.35 g, 24%).; Mass Spec FIA MS 401; $^1$H NMR(CDCl$_3$, 500 MHz) δ7.42(d,1H), 7.14(m,1H), 7.03(m,1H), 6.95(m,1H), 6.35(d,1H), 3.52(t,2H), 3.25(t,2H), 1.82-1.90(m,4H), 1.49 (s,9H).

Example 34

(4-(5-(2,3-Difluorophenyl)-1H-1,2,3-triazol-4-yl)-1H-pyrrol-2-yl)(pyrrolidin-1-yl)methanone. (4-(2-(2,3-difluorophenyl)ethynyl)-1-BOC-pyrrol-2-yl)(pyrrolidin-1-yl) methanone (0.2 g, 0.5 mmol) was dissolved in trimethylsilylazide (3 mL) and heated at 150° C. for 18 hr. The solvent was evaporated and the crude product was purified by Biotage HPFC system (100% EtOAC) to afford title compound as a brown foam (0.019 g, 11%).; Mass Spec FIA MS 344; $^1$H NMR(CDCl$_3$, 500 MHz) 10.05(s,1H), 7.06-7.25(m, 3H), 6.98(s,1H), 6.71(s,1H),3.55-3.60(m,4H), 1.79-1.95(m,4H).

Example 35

4-[5-Amino-4-(2,3-dichloro-phenyl)-4H-[1,2,4]triazol-3-yl]-1H-pyrrole-2-carboxylic acid. To a solution of 4-[N-(2,3-dichloro-phenyl)-N'-amino-carbamimidoyl]-1-methanesulfonyl-1H-pyrrole-2-carboxylic acid methyl ester (Prepared by the same method described above for the preparation of the corresponding difluoro compound) (150 mg, 0.37 mmol) in MeOH (2 mL) was added BrCN (60 mg, 0.57 mmol) at RT. The mixture was stirred at RT for 12 h. The solvent was removed by evaporation, the residue was dissolved in MeOH (4 mL), and the resulting solution was treated with 6N NaOH (1 mL) at 50° C. for 4 h. After cooling to RT, the solution was acidified with 6N HCl. The organic solvent was evaporated, the remaining aqueous solution was diluted with CH3CN, and the inorganic salt was removed by filtration. The filtrate was concentrated under vacuum to give a crude product, which was purified by HPLC for next reaction. MS (ES+): m/e=338.0 (M+H); LC: 2.44 min.

Example 36

{4-[5-Amino-4-(2,3-dichloro-phenyl)-4H-[1,2,4]triazol-3-yl]-1H-pyrrol-2-yl}-(2,5-dihydro-pyrrol-1-yl)-methanone (I-43). To a solution of 4-[5-amino-4-(2,3-dichloro-phenyl)-4H-[1,2,4]triazol-3-yl]-1H-pyrrole-2-carboxylic acid (10 mg, 0.03 mmol) in DMA (1 mL) was added CDI (6 mg, 0.04 mmol). The solution was stirred at RT for 30 min before the addition of 2,5-dihydro-1H-pyrrole (6 mg, 0.09 mmol). The reaction mixture was stirred at RT for another 60 min and purified by Gilson HPLC directly to afford a white solid (7.5 mg, 64%). MS (ES+): m/e=389.2 (M+H); LC: 2.65 min.

Example 37

4-[5-Amino-4-(2,3-dichloro-phenyl)-4H-[1,2,4]triazol-3-yl]-1H-pyrrole-2-carboxylic acid (3-imidazol-1-yl-propyl)-amide. Prepared by the same method used for the preparation of {4-[5-Amino-4-(2,3-dichloro-phenyl)-4H-[1,2,4]triazol-3-yl]-1H-pyrrol-2-yl}-(2,5-dihydro-pyrrol-1-yl)-methanone White solid (13 mg, 90%). MS (ES+): m/e=445.1 (M+H); LC: 2.31 min.

Example 38

1-Methanesulfonyl-4-nitro-1H-pyrrole-2-carboxylic acid ethyl ester. To a solution of 4-nitro-1H-pyrrole-2-carboxylic acid ethyl ester (from TCI-US) (6 g, 32.6 mmol) in 120 mL of anhydrous THF was added NaH (1.56 g, 39.0 mmol) at 0° C. The suspension was then stirred at room temperature for 1 h before addition of MsCl (5.6 g, 48.9 mmol). The mixture was left at RT for overnight and then poured into 2N HCl solution (100 mL). The aqueous solution was extracted with EtOAc (3×60 mL), the combined organic layers were dried over MgSO4, the solvent was removed by evaporation, and the residue was dried on the oil pump to give a pale-yellow solid (8.0 g, 94%). MS (ES+): m/e=263.3 (M+H); LC: 3.27 min.

Example 39

4-(2,3-Difluoro-benzoylamino)-1-methanesulfonyl-1H-pyrrole-2-carboxylic acid ethyl ester. To a solution of 4-amino-1-methanesulfonyl-1H-pyrrole-2-carboxylic acid ethyl ester (1 g, 4.3 mmol) and triethylamine (650 mg, 6.4 mmol) in dry $CH_2Cl_2$ (20 mL) was added 2,3-difluoro-benzoyl chloride (760 mg, 4.3 mmol). The mixture was stirred at RT for 3 h and diluted with EtOAc (150 mL). After washing with 2N HCl (80 mL) and $NaHCO_3$ (2×80 mL), the organic layer was dried over MgSO4, filtered, and evaporated to give a yellow solid (1.3 g, 81%). This solid was dried on the vacuum pump for 14 hrs and then was used for the next step directly. MS (ES+): m/e=373.2 (M+H); LC: 3.45 min.

Example 40

4-(3-(2,3-difluorophenyl)-4H-1,2,4-triazol-4-yl)-N-(((S)-tetrahydrofuran-2-yl)methyl)-1H-pyrrole-2-carboxamide. 4-(2,3-Difluoro-benzoylamino)-1-methanesulfonyl-1H-pyrrole-2-carboxylic acid ethyl ester was converted to title compound using the same procedures as described above for the preparation of triazole compounds. (28 mg, 55%). MS (ES+): m/e=374.2 (M+H); LC: 2.68 min.

Example 41

N-(3-(1H-imidazol-1-yl)propyl)-4-(3-(2,3-difluorophenyl)-4H-1,2,4-triazol-4-yl)-1H-pyrrole-2-carboxamide (I-44). Prepared similarly (24 mg, 44%). Colorless syrup. MS (ES+): m/e=398.2 (M+H); LC: 2.35 min.

Example 42

$K_i$ Determination for the Inhibition of c-Met

Compounds were screened for their ability to inhibit c-Met kinase activity using a standard coupled enzyme system (Fox et al., *Protein Sci.* 1998, 7, 2249). Reactions were carried out in a solution containing 100 mM HEPES (pH 7.5), 10 mM $MgCl_2$, 25 mM NaCl, 300 µM NADH, 1 mM DTT, and 1.5% DMSO. Final substrate concentrations in the assay were 200 µM ATP (Sigma Chemicals, St Louis, Mo.) and 10 µM polyGluTyr (Sigma Chemical Company, St. Louis). Reactions were carried out at 30° C. and 80 nM c-Met. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and a test compound of the present invention. The assay stock buffer solution (175 µl) was incubated in a 96 well plate with 5 µl of the test compound of the present invention at final concentrations spanning 0.006 µM to 12.5 µM at 30° C. for 10 minutes. Typically, a 12-point titration was conducted by preparing serial dilutions (from 10 mM compound stocks) with DMSO of the test compounds of the present invention in daughter plates. The reaction was initiated by the addition of 20 µl of ATP (final concentration 200 µM). Rates of reaction were obtained using a Molecular Devices Spectramax plate reader (Sunnyvale, Calif.) over 10 minutes at 30° C. The $K_i$ values were determined from the rate data as a function of inhibitor concentration.

Compounds of the present invention were found to be inhibitors of c-Met. Compounds I-4, I-10, I-16, I-24, I-38, I-39, I-40, I-41, I-46, and I-47 were found to inhibit with a $K_i$ of 1-10 µM. Compounds I-37, I-44, and I-49 were found to inhibit with a Ki of >10 µM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

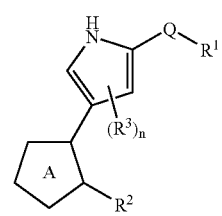

or a pharmaceutically acceptable salt thereof, wherein:
Q is —C(O)N(R)—, —C(O)—, or —C(O)O—;
  each R is independently hydrogen or an optionally substituted $C_{1-6}$ aliphatic group, wherein:
    two R groups on the same nitrogen atom are optionally taken together with said nitrogen atom to form an optionally substituted 3-7 membered saturated, partially unsaturated, or fully unsaturated ring having 1-3 heteroatoms independently selected from nitrogen, oxygen, or sulfur;
  $R^1$ is H, —N(R)$_2$, or an optionally substituted ring selected from a 3-7 membered saturated or partially unsaturated ring having 0-3 heteroatoms independently selected from nitrogen, oxygen, or sulfur, a 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur;
  $R^2$ is an optionally substituted 6-membered aryl ring having 0-3 nitrogens;
  each $R^3$ is independently R, CN, NO$_2$, halogen, N(R)$_2$, OR, or SR;
  n is 0-2; and
  Ring A is

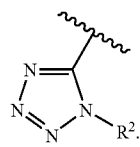

2. The compound according to claim 1, wherein:
$R^1$ is an optionally substituted ring selected from a 3-7 membered saturated or partially unsaturated ring having 0-3 heteroatoms independently selected from nitrogen, oxygen, or sulfur, a 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur.

3. The compound according to claim 2, wherein:
$R^1$ is an optionally substituted 4-6 membered saturated ring having 0-3 heteroatoms independently selected from nitrogen, oxygen, or sulfur.

4. The compound according to claim 2, wherein:
$R^1$ is an optionally substituted 5-6 membered aryl ring having 0-4 heteroatoms independently selected from nitrogen, oxygen, or sulfur, or an 8-10 membered bicyclic partially unsaturated or aryl ring having 0-4 heteroatoms independently selected from nitrogen, oxygen, or sulfur.

5. The compound according to claim 1, wherein Q is —C(O)N(R)—.

6. The compound according to claim 1, wherein Q is —C(O)—.

7. The compound according to claim 1, wherein n is 0.

8. The compound according to claim 1, wherein n is 1.

9. The compound according to claim 1, wherein $R^2$ is an optionally substituted phenyl ring.

10. The compound according to claim 1, wherein $R^2$ is an optionally substituted pyridyl or pyrimidinyl ring.

11. A compound selected from the group consisting of:

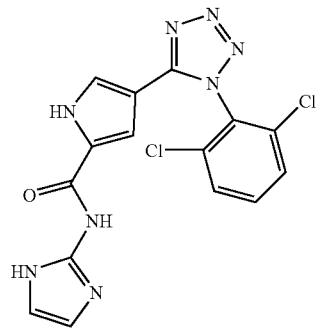

I-21

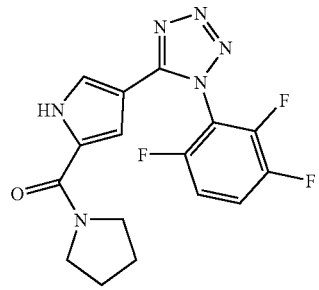

I-22

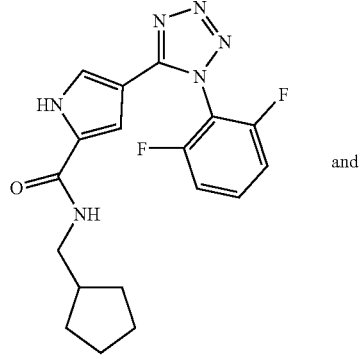

I-23 and

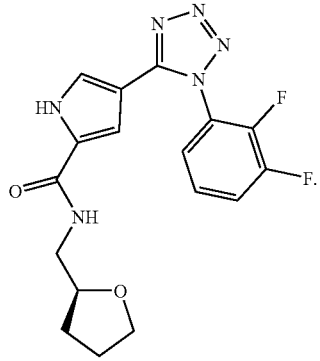

I-24

12. A composition comprising a compound according to claim 1, and a pharmaceutically acceptable carrier, adjuvant, or vehicle.

13. The composition according to claim 12, additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating liver disease, an anti-viral agent, an agent for treating blood disorders, or an agent for treating immunodeficiency disorders.

14. A method of inhibiting c-Met kinase activity in a biological sample selected from a cell culture, biopsied material obtained from a mammal, saliva, urine, feces, semen, tears, or extracts thereof; said method comprising contacting said biological sample with a compound according to claim 1 or a composition comprising said compound.

* * * * *